United States Patent
Perryman et al.

(10) Patent No.: US 11,027,139 B2
(45) Date of Patent: Jun. 8, 2021

(54) MINIATURE IMPLANTABLE DEVICE AND METHODS

(71) Applicant: Stimwave Technologies Incorporated, Pompano Beach, FL (US)

(72) Inventors: Laura Tyler Perryman, Miami Beach, FL (US); Chad Andresen, Miami Beach, FL (US)

(73) Assignee: Stimwave Technologies Incorporated, Pompano Beach, FL (US)

(*) Notice: Subject to any disclaimer, the term of this patent is extended or adjusted under 35 U.S.C. 154(b) by 226 days.

(21) Appl. No.: 16/247,831

(22) Filed: Jan. 15, 2019

(65) Prior Publication Data

US 2019/0143124 A1    May 16, 2019

Related U.S. Application Data

(60) Division of application No. 14/775,306, filed as application No. PCT/US2014/029726 on Mar. 14, (Continued)

(51) Int. Cl.
*A61N 1/375* (2006.01)
*A61N 1/372* (2006.01)
(Continued)

(52) U.S. Cl.
CPC ....... *A61N 1/3756* (2013.01); *A61N 1/37205* (2013.01); *A61B 5/0031* (2013.01);
(Continued)

(58) Field of Classification Search
CPC ............ A61N 1/36071; A61N 1/37205; A61N 1/3756; A61N 1/3787; A61B 5/0031; A61B 5/04001; A61B 5/4836
See application file for complete search history.

(56) References Cited

U.S. PATENT DOCUMENTS 6,323,256 B1   11/2001   DelMain
6,421,569 B1   7/2002    Treaba et al.
(Continued)

FOREIGN PATENT DOCUMENTS

WO   WO2010114836   10/2010
WO   WO2012138782   4/2011
(Continued)

OTHER PUBLICATIONS

International Search Report and Written Opinion in PCT/US2014/029726, dated Aug. 22, 2014, 26 pages.

*Primary Examiner* — Christopher A Flory
(74) *Attorney, Agent, or Firm* — Fish & Richardson P.C.

(57) ABSTRACT

A method for treating neurological pain includes inserting an introducer needle of gauge 18 or smaller through a percutaneous incision site on a body, coupling a first mating feature at a distal end of an elongate member of a stylet to a second mating feature of an implantable device that is configured to receive a wireless signal and to generate one or more electrical pulses from the wireless signal for exciting a tissue within the body, advancing the stylet and the implantable device together as an assembly to the tissue within the body through a lumen of the introducer needle, and applying the one or more electrical pulses to one or more electrodes of the implantable device to modulate the tissue within the body.

16 Claims, 20 Drawing Sheets

Related U.S. Application Data 2014, now Pat. No. 10,245,436, which is a continuation-in-part of application No. PCT/US2013/073326, filed on Dec. 5, 2013.

(60) Provisional application No. 61/786,098, filed on Mar. 14, 2013, provisional application No. 61/733,867, filed on Dec. 5, 2012.

(51) Int. Cl.
    *A61N 1/36*     (2006.01)
    *A61N 1/378*     (2006.01)
    *A61B 5/00*     (2006.01)
    *A61B 5/24*     (2021.01)

(52) U.S. Cl.
    CPC ............... *A61B 5/24* (2021.01); *A61B 5/4836* (2013.01); *A61N 1/36071* (2013.01); *A61N 1/3787* (2013.01)

(56) References Cited

U.S. PATENT DOCUMENTS

| | | |
|---|---|---|
| 6,774,157 B2 | 8/2004 | DelMain |
| 7,187,984 B2 | 3/2007 | Lau |
| 7,328,071 B1 * | 2/2008 | Stehr .................... A61N 1/0587 600/585 |
| 7,799,037 B1 | 9/2010 | He |
| 7,949,395 B2 | 5/2011 | Kuzma |
| 8,099,171 B2 | 1/2012 | Indravudh |
| 8,192,787 B2 | 6/2012 | Kirby |
| 8,834,657 B2 | 9/2014 | Claude |
| 9,212,981 B2 | 12/2015 | Mercer |
| 2002/0055761 A1 | 5/2002 | Mann |
| 2002/0111393 A1 | 8/2002 | DelMain |
| 2003/0040671 A1 | 2/2003 | Somogyi |
| 2004/0127942 A1 | 7/2004 | Yomtov |
| 2004/0249417 A1 | 12/2004 | Ransbury |
| 2004/0260346 A1 | 12/2004 | Overall |
| 2005/0043765 A1 | 2/2005 | Williams |
| 2005/0058701 A1 | 3/2005 | Gross |
| 2005/0137668 A1 | 6/2005 | Khan |
| 2006/0009831 A1 | 1/2006 | Lau |
| 2006/0020299 A1 | 1/2006 | Shaky |
| 2006/0224225 A1 | 10/2006 | Ransbury |
| 2007/0032749 A1 | 2/2007 | Overall |
| 2007/0066995 A1 | 3/2007 | Strother |
| 2007/0067000 A1 | 3/2007 | Strother |
| 2007/0244290 A1 | 10/2007 | Swanson |
| 2007/0265543 A1 | 11/2007 | VanSickle |
| 2008/0058886 A1 | 3/2008 | Williams |
| 2008/0063703 A1 | 3/2008 | Gross |
| 2008/0065051 A1 | 3/2008 | Williams |
| 2008/0077219 A1 | 3/2008 | Williams |
| 2008/0132961 A1 | 6/2008 | Jaax |
| 2008/0154327 A1 | 6/2008 | Ransbury |
| 2009/0062883 A1 | 3/2009 | Meadows |
| 2009/0069803 A1 | 3/2009 | Starkebaum |
| 2009/0171408 A1 | 7/2009 | Solem |
| 2009/0204063 A1 | 8/2009 | Policker |
| 2009/0204170 A1 | 8/2009 | Hastings |
| 2009/0234407 A1 | 9/2009 | Hastings |
| 2010/0010565 A1 | 1/2010 | Lichtenstein |
| 2010/0174340 A1 | 7/2010 | Simon |
| 2010/0179562 A1 | 7/2010 | Linker et al. |
| 2010/0198316 A1 | 8/2010 | Toselli |
| 2010/0331934 A1 | 12/2010 | McDonald |
| 2010/0331940 A1 | 12/2010 | Indravudh |
| 2011/0118814 A1 | 5/2011 | Cole |
| 2011/0160557 A1 | 6/2011 | Cinbis |
| 2011/0160801 A1 | 6/2011 | Markowitz |
| 2011/0270339 A1 | 11/2011 | Murray, III |
| 2011/0270340 A1 | 11/2011 | Pellegrini |
| 2011/0288615 A1 | 11/2011 | Armstrong |
| 2012/0043011 A1 | 2/2012 | Claude |
| 2012/0059389 A1 | 3/2012 | Larson |
| 2012/0095539 A1 | 4/2012 | Khairkhahan |
| 2012/0116489 A1 | 5/2012 | Khairkhahan |
| 2012/0188042 A1 | 7/2012 | Claude |
| 2012/0191150 A1 | 7/2012 | Kameli |
| 2013/0096602 A1 | 4/2013 | Kumar |
| 2013/0110127 A1 | 5/2013 | Bornzin |
| 2013/0116738 A1 | 5/2013 | Samade |
| 2013/0116740 A1 | 5/2013 | Bornzin |
| 2013/0131591 A1 | 5/2013 | Berthiaume |
| 2013/0197609 A1 | 8/2013 | Moore |
| 2013/0218229 A1 | 8/2013 | Sharma |
| 2013/0226260 A1 | 8/2013 | Brenner |
| 2014/0018818 A1 | 1/2014 | Somogyi |
| 2014/0107723 A1 | 4/2014 | Hou |
| 2014/0172048 A1 | 6/2014 | Kameli |
| 2014/0172060 A1 | 6/2014 | Bornzin |
| 2014/0277312 A1 | 9/2014 | Bornzin |
| 2014/0309708 A1 | 10/2014 | Sharma |
| 2015/0005680 A1 | 1/2015 | Lipari |
| 2015/0127068 A1 | 5/2015 | Simon |
| 2015/0202431 A1 | 7/2015 | Bornzin |
| 2015/0297900 A1 | 10/2015 | Perryman |
| 2016/0015988 A1 | 1/2016 | Perryman |
| 2016/0023003 A1 | 1/2016 | Perryman |
| 2016/0023005 A1 | 1/2016 | Perryman |
| 2016/0038741 A1 | 2/2016 | Perryman |
| 2016/0067494 A1 | 3/2016 | Lipari |
| 2016/0074661 A1 | 3/2016 | Lipari |
| 2016/0144180 A1 | 5/2016 | Simon |

FOREIGN PATENT DOCUMENTS

| | | |
|---|---|---|
| WO | WO2012021976 | 2/2012 |
| WO | WO2012126003 | 3/2012 |

* cited by examiner

MINIATURE IMPLANTABLE DEVICE AND METHODS

CROSS REFERENCE TO RELATED APPLICATIONS

This application is a divisional of U.S. patent application Ser. No. 14/775,306, filed Sep. 11, 2015, now allowed, which is a national phase application of International Application No. PCT/US2014/029726, filed Mar. 14, 2014, which claims benefit of U.S. Provisional Patent Application Ser. No. 61/786,098, filed Mar. 14, 2013. Under 35 U.S.C. §§ 365 and 120, PCT/US2014/029726 claims the benefit of, and is a continuation in part of, International Application No. PCT/US2013/073326, filed Dec. 5, 2013, which claims the benefit of U.S. Provisional Application Ser. No. 61/733,867, filed Dec. 5, 2012. The disclosures of the prior applications are incorporated by reference herein in their entirety for all purposes.

TECHNICAL FIELD

This application relates generally to implantable stimulators.

BACKGROUND

Modulation of excitable tissue in the body by electrical stimulation has become an important type of therapy for patients with chronic disabling conditions, including chronic pain, problems of movement initiation and control, involuntary movements, vascular insufficiency, heart arrhythmias and more. A variety of therapeutic intra-body electrical stimulation techniques can treat these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing. Typically, such devices utilize a subcutaneous battery operated implantable pulse generator (IPG) to provide power or other charge storage mechanisms.

SUMMARY

In one aspect, some implementations provide an implantable wirelessly powered device that includes: one or more electrodes configured to apply one or more electrical pulses to an excitable tissue; and a first antenna configured to: receive, from a second antenna and through electrical radiative coupling, an input signal containing electrical energy, the second antenna being physically separate from the implantable device; and one or more circuits electrically connected to the first antenna, the circuits configured to: create the one or more electrical pulses suitable for stimulation of excitable tissue using the electrical energy contained in the input signal; and supply the one or more electrical pulses to the one or more electrodes, wherein the implantable device is shaped and arranged for delivery into a patient's body through an introducer or a needle of 18 gauge or smaller.

Implementations may include the following features. The one or more electrodes may include at least one recording electrode configured to sense neural activity of the subject. The one or more circuits may be further configured to generate a recorded electrical signal encoding the sensed neural activity. The first antenna may be further configured to transmit the recorded electrical signal to the second antenna using the electrical energy contained in the input signal.

The electrodes may include two (2) to twenty four (24) electrodes, each having a longitudinal length between 0.25 and 6.0 mm and a diameter between 0.1 and 0.8 mm. The electrodes are spaced between 1 mm to 6 mm apart and have a combined surface area of between 0.06 $mm^2$ to 60.00 $mm^2$. The implantable device may be in a paddle style form factor. The implantable device may have a height between 0.1 mm and 0.8 mm, and a width between 0.5 mm and 0.8 mm. The implantable device may be shaped concavely to secure a lateral position on the excitable tissue after the implantable device has been delivered into the patient's body.

In another aspect, some implementations provide a device that includes a stylet comprising a mating feature at a distal end thereof; and an implantable device with a cylindrical body comprising a mating feature at a proximal end thereof, the mating feature of the implantable device configured to mate with the mating feature of the stylet to form a subassembly; wherein the subassembly of the stylet and implantable device with a cylindrical body is sized and shape for delivery into a subject's body through an introducer or needle that is 18 gauge or smaller.

Implementations may include one or more of the following features. The stylet may include a placement stylet. The mating feature of the stylet may include a protrusion and the mating feature of the implantable device includes an indentation, the protrusion being configured to mate with the indentation. The stylet may include a suction stylet, the suction stylet including an inner plunger in a shaft, a suction tip, and an air chamber between the suction tip and a distal end of the inner plunger. The stylet may mate with the implantable device when a sliding motion of the inner plunger in the shaft creates a negative pressure in the air chamber to engage the suction tip with the mating feature on the implantable device.

In yet another aspect, some implementations may provide a method for treating neurological pain, including: placing an introducer through an incision site on a patient, the introducer including a needle that is 18 gauge or less; advancing a first implantable device to a target site in the patient's body through the introducer and causing an electrical impulse to be applied to one or more electrodes within the implantable device to modulate excitable tissue at the target site within the patient's body.

Implementations may include one or more of the following features. Advancing the first implantable device may include: advancing a wirelessly powered implantable device that includes: a first antenna configured to: receive, from a second antenna and through electrical radiative coupling, an input signal containing electrical energy, the second antenna being physically separate from the implantable device; and one or more circuits electrically connected to the first antenna, the circuits configured to: create the one or more electrical pulses suitable for stimulation of the excitable tissue using the electrical energy contained in the input signal; and supply the one or more electrical pulses to the one or more electrodes.

The method may further include mating the implantable device with a stylet. Advancing the implantable device may include advancing the miniature implantable device mated with the stylet through the introducer. Mating the implantable device with a stylet may include mating the miniature implantable device with a placement stylet. Mating the implantable device with a stylet may include mating the implantable device with a suction stylet. The method may further include activating the suction stylet by pulling a plunger in the suction stylet to create a negative pressure in an air chamber of the suction stylet so that the suction stylet is mated with the implantable device. Advancing the implantable device may further include advancing the implantable device mated with the suction stylet. The method may further include withdrawing the implantable device mated with the suction stylet. The method may further include: advancing a second implantable device to the target site in the patient's body through the introducer; and causing a second electrical impulse to be applied to one or more electrodes within the second implantable device to modulate one or more excitable tissue at the target site within the patient's body.

In one aspect, an implantable device or recording device includes an enclosure shaped and configured for percutaneous delivery into a patient's body through an introducer. The enclosure houses one or more electrodes configured to apply one or more electrical pulses to an excitable tissue or record neural activity from tissue. The enclosure preferably also houses a first antenna configured to receive, from a second antenna through electrical radiative coupling, an input signal containing electrical energy. In the preferred embodiments, the second antenna is physically separate from the wirelessly powered device and may be positioned external to the patient's body. In some cases, the first antenna is a dipole antenna. The enclosure further includes one or more circuits electrically connected to the first antenna and configured to create the electrical energy contained in the input signal and to supply the electrical energy to the one or more electrodes or to circuits to enable the conversion of the recording signals from the electrodes. The first antenna can also be configured to transmit the data signals from the on-board diagnostics or recordings.

In one configuration, a portion of the enclosure may leave the electrodes in a non-direct contact with the excitable tissue after the implantable device has been delivered into the subject's body. The enclosure can be semi-cylindrical in shape and the electrodes may include at least one directional electrode that directs a current path associated with the one or more electrical pulses to a direction that is substantially perpendicular to the neural tissue. The electrodes may include a semi-cylindrical array of electrodes. The electrodes may be made of at least one of platinum, platinum-iridium, gallium-nitride, titanium-nitride, iridium-oxide, or combinations thereof. The electrodes may include between two (2) to twenty-four (24) electrodes, each having a longitudinal length from between about 0.25 and 6.0 mm and a diameter from between about 0.1 and 0.8 mm. The electrodes are spaced between about 0.25 mm to 6 mm apart and have a combined surface area from between about 0.06 mm$^2$ to 250.0 mm$^2$.

In another aspect, a method for treating a patient with a disorder or chronic condition comprises positioning a miniature device into the patient's body. In certain cases, the device is advanced percutaneously through a needle, such as, for example, a tuohy needle, no larger than 18 gauge. The device may be delivered to excitable tissue innervated by central and peripheral nerves and their plexuses or downstream branches such as the cochlear, cranial, trigeminal, occipital, radius, ulnar, vagus, celiac, cervical, spinal, lumbar, sacral, sciatic, femoral, or brachial nerves or deep brain structures, and cortical surfaces of the brain containing sensory or motor nerves.

The enclosure may have an external coating of biocompatible polymer, the polymer includes at least one of: polymethymethacrylate (PMMA), polydimethylsiloxane (PDMS), parylene, polyurethance, polytetrafluoroethylene (PTFE), or polycarbonate. The enclosure may further have an external coating of silicone elastomer. The enclosure can further house antenna coupling contacts, the antenna contacts being electrically connected to the antennas and the circuit and configured to couple the antenna with the surrounding tissue. The antenna coupling contacts can include from between two to eight antenna-coupling pairs. The antenna coupling contacts may be located proximal, relative to the electrodes, in the enclosure. The antenna coupling contacts can each have a longitudinal length of between about 0.1 mm and 6.0 mm, and a width of between about 0.1 mm to 0.8 mm. The antenna coupling contacts can be spaced between about 5 mm and 80 mm apart. At least one of the antennas can be constructed as a conductive trace contained on one of the circuits. At least one of the antennas can be fabricated as a conductive wire connected to one of the circuits. The circuits can be flexible circuits. The flexible circuits may be placed proximal, relative to the electrodes, in the enclosure.

In yet another aspect, a stylet is configured to aid in the surgical placement of a miniature device. The stylet fits through the inner diameter of a tuohy needle no greater than 18 gauge, and may contain a feature for mating the stylet to a miniature implantable device. On the distal tip of the stylet is a mating feature, which may be semi-spherical, and grips the miniature implantable device during placement. Other features may include alternative extruded shapes for mating the stylet to the miniature device. The mating feature may only extrude from the distal tip of the stylet from between about 0.1 mm and 1.0 mm and does not fill the body of the device. In some cases, the mate between the miniature device and the stylet is active only during distal directional movement of the stylet. The stylet may have a longitudinal length of between about 50 mm and 177 mm. The stylet may have a diameter in the range from between about 0.1 mm and 0.9 mm. The stylet may be made of a rigid biocompatible material such as stainless steel, titanium, nylon, or polyethylene. The mating feature may have a surface material that allows for increased friction such as silicon or polyurethane to improve the mate between the stylet and the miniature device.

Some implementations of the stylet include a central lumen that contains a plunger used for creating a negative pressure port on the distal tip. The negative pressure port exits where the mating feature connects to the miniature device. This suction stylet can grip the miniature device during distal and proximal directional movement. The suction stylet may have a locking feature that allows for the plunger pressure level to be maintained without the operator maintaining the force on the plunger.

Some implementations provide a method of treating neurological pain. The method may include providing a miniature device including: an enclosure that houses one or more electrodes; a first antenna configured to receive, from a second antenna and through electrical radiative coupling, an input signal containing electrical energy, the second antenna being physically separate from the implantable device; one or more flexible circuits electrically connected to the first antenna, the flexible circuits configured to convert the electrical energy contained in the input signal to a power source to supply energy to one or more electrodes, or to power recording circuitry connected to one or more recording electrodes; and implanting the device into a subject's body through an introducer.

In another aspect, a system for stimulating excitable tissue includes a controller module having a first antenna external to the patient's body and configured to send an input signal containing electrical energy to a second antenna through electrical radiative coupling. The second antenna is a dipole antenna and is located in an enclosure in a miniature device, such as those described above. The miniature device may not include an internal power source. The circuits of the device may include only passive components. The input signal has a carrier frequency in the range of about 300 MHz to about 8 GHz, preferably between about 750 MHz to about 2.8 GHz.

DETAILED DESCRIPTION

In various implementations, an implanted neural stimulation device can send electrical stimulation to targeted excitable tissue by using electrical energy received without the use of cables or inductive coupling. In particular, remote radio frequency (RF) energy can be transmitted and used to provide power to the implanted device. The implanted device can be used in the treatment of pain or a variety of other modalities. The device may be placed nearby excitable tissue innervated by central and peripheral nerves and their plexuses or downstream branches (such as, for example, the cochlear, cranial, trigeminal, occipital, radius, ulnar, vagus, celiac, cervical, spinal, lumbar, sacral, sciatic, femoral, or brachial nerves or deep brain structures, and cortical surfaces of the brain containing sensory or motor nerves).

The implantable device includes an enclosure that houses one or more conductive antennas (for example, dipole or patch antennas), internal electronic circuitry for waveform and electrical energy rectification, and one or more electrode pads allowing for neural stimulation of excitable tissue or recording of neural activity in a surrounding tissue.

Various implementations can include distinct advantages over wired leads in regards to ease of insertion, cross connections, elimination of extension wires, and no requirement for an implantable pulse generator in order to administer a chronic therapy. Various implementations also may have an associated lower overall cost compared to existing implantable neural modulation systems due to the elimination of the implantable pulse generator and this may lead to wider adoption of neural modulation therapy for patients as well as reduction in overall cost to the healthcare system.

Figure 1:
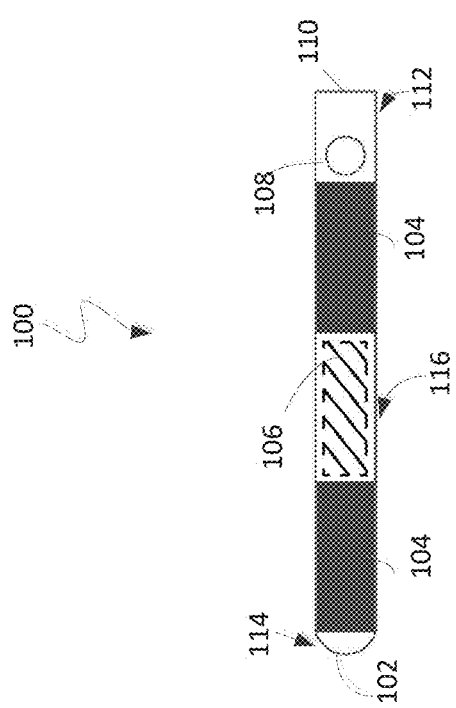
FIG. 1 illustrates an example of a miniature implantable device including wireless power receiving electronics.

FIG. 1 illustrates an example miniature implantable device 100. The implantable device 100 includes a body 116 with a distal end 114 and a proximal end 112.

The distal end 114 includes a rounded tip 102. The distal end 114 of the miniature wireless device body 116 may include a non-conductive tip 102 that is rounded with a length of between about 0.5 mm and about 1.0 mm, with a smooth finish for navigating the device through tissue.

The device body 106 includes electrodes 104 and houses electronic circuitry 106. In some implementations, the miniature implantable device may have between one and twenty-four cylindrical electrodes 104 on its distal end 114 with a diameter between about 0.1 mm and about 0.8 mm for stimulation applications. The diameters and other sizes may, of course, vary from one target treatment to another target treatment. The electrodes 104 may have a longitudinal length of between about 0.25 mm and about 6.0 mm from the distal end 114 toward the proximal end 112. The spacing between the electrode contacts may be between about 0.25 mm and about 6.0 mm. The total electrode surface area of the cylindrical wireless lead body may be between about 0.06 mm$^2$ and about 250.0 mm$^2$.

The proximal end 112 includes a suturing feature 108 and a mating feature 110. The suturing feature 108 is a passage through the proximal end with a central axis that is parallel to a longitudinal axis of the device body 106. Suturing feature 108 may allow a clinician to suture and anchor implantable device 100 during an implantation procedure. For instance, suture can be passed through the passage of suturing feature 108 and tied to tissue. In some cases, the implantable device 100 can be sutured to the surrounding tissue. Suturing the implantable device may reduce mobility and improve stability of the implanted device.

Mating feature 110 may allow the device 100 to be mechanically mated with a stylet, as disclosed herein. In one configuration, mating feature 110 is a concave indentation that extends along a longitudinal axis of the device body 106 from the proximal end 112. The concave indentation mates with a corresponding feature on a placement stylet or suction stylet. The concave stylet-mating feature on the proximal end 110 of implantable device 100 can have, for example, a length of between about 0.1 mm and 1.0 mm. In other configurations, the stylet-mating feature 110 may be semi-spherical or asymmetrical in shape for improved steerability of the device during implantation.

The various devices described herein, including device 100, may include, for example, anywhere from one to twenty-four electrodes 104, any of which can be designated by a programmer user as either a cathode or an anode. For example, electrodes 104 can include multiple cathodes coupled to the targeted tissue as well as at least one anode. The electrode array can receive electrical stimulation pulses ranging from about 0 to about 10 V peak amplitude at a pulse width up to about 1 millisecond. Such stimulation pulses may be from a single receiver element within the device body. The polarity of the electrodes can produce various volume conduction distributions from the cathodes to the anodes to inhibit or excite surrounding excitable tissue, which may include A-δ and/or primary or secondary c-fiber afferents. To reduce electrode impedance, the electrodes may be made of a conductive, corrosion resistant, biocompatible material such as, for example, platinum, platinum-iridium, gallium-nitride, titanium-nitride, or iridium-oxide.

The miniature implantable device 100 may be 0.8 mm diameter or smaller. Miniature implantable device 100 may receive microwave or RF energy from an external source non-inductively and without a wire. The miniature implantable 100 device may contain the circuitry necessary to receive the pulse instructions from a source external to the body.

In particular, electronic circuitry 106 of the miniature implantable device may convert an input signal received at the one or more antennas into an electrical energy and electrical pulses. In some implementations, extension tubing can provide an enclosure that houses, for example, flex circuitry. In some embodiments, the electronic circuitry 106 may include one or a plurality of diodes that function to rectify the wireless signal, such as a sinusoidal signal, picked up by the non-inductive antenna(s). The diodes have a low threshold voltage to maximize the energy used for creating waveforms and power. Additionally, internal circuitry 106 may include a charge balancing microelectronic component to reduce or prevent corrosion as well as a current limiter.

In certain embodiments, the electronic circuitry 106 may include one or more non-inductive antennas, a rectifier, a charge balancer, a current limiter, a controller, and a device interface. In brief, the rectifier functions to rectify the signal received by the one or more non-inductive antennas. The rectified signal may provide power to electrodes 104. The rectified signal may also be fed to a charge balance component that is configured to create one or more electrical pulses such that the one or more electrical pulses result in a substantially zero net charge (that is, the pulses are charge balanced). The charge balanced pulses are passed through the current limiter to the electrode interface, which applies the electrical pulses to electrodes 104.

In some implementations, an internal dipole (or other) antenna configuration(s) may be used in lead 100 to receive RF power through electrical radiative coupling. This coupling mechanism can allow such devices to produce electrical currents capable of stimulating nerve bundles without a physical connection to an implantable pulse generator (IPG) or use of an inductive coil. In some implementations, between two to eight tissue-exposed-ring-antenna coupling contacts may be proximal to the electrodes. The tissue-exposed-ring-antenna coupling contacts may have a longitudinal length of between about 0.25 mm and about 6.0 mm from the distal end 114 toward the proximal end 110. The spacing between the tissue-exposed ring antenna coupling contacts may be between about 5 mm and about 80 mm. In certain implementations, tissue-exposed-small-antenna coupling contacts with a diameter between about 0.2 mm and about 0.6 mm may be used in lieu of the tissue-exposed-ring-antenna coupling contacts.

In some implementations, at least one of the antennas can be constructed as a conductive trace feature contained on one of the circuits. In other implementations, at least one of the antennas can be fabricated as a conductive wire connected to one of the circuits. In various implementations, implantable device 100 my employ non-inductive, for example, dipole or other antenna configuration(s), to receive RF power through electrical radiative coupling.

For context, neural stimulating devices may utilize a battery-powered or charge-storage component. Such devices are no longer functional once the battery cannot be recharged or charge cannot be stored. Consequently, for an implanted device, a patient would need to undergo a subsequent surgical procedure to obtain a functional replacement device.

In contrast, some implementations disclosed herein do not rely upon battery power or charge storage for operation. In some configurations, the implantable device can receive electrical power from radiated RF energy non-inductively and without a wired connection. As a result, the life of an implanted device is no longer limited by the life of the battery or ability to store charge.

Further, the electrical radiative coupling mechanism (for example, a dipole antenna) can be utilized to improve the form factor of the miniature implanted device and allow for miniature diameters. Electrical radiative coupling may also allow for the transmission and reception of energy at greater depths with less degradation in efficiency than inductive coil techniques. This electrical radiative coupling can provide an advantage over devices that employ inductive coupling where the efficiency of such implants may be highly dependent on the distance separating the external transmitter coil and the implanted receiver coil.

Accordingly, some implementations disclosed herein do not include inductive loops to receive RF energies in a wireless manner. Instead, some implementations disclosed herein use electric radiative coupling to receive RF energies. Such implementations facilitate a smaller form factor for a fully functional implantable electrical stimulation or recording device. The improved form factor may result in a less invasive surgical procedure for placement of the device. The improved form factor may also decrease scarring the amount of bodily tissue in contact with the implanted device is reduced.

A telemetry signal may be transmitted by the miniature implantable device 100 to deliver information to an external controller. The telemetry signal may be sent by modulation of a carrier signal. The telemetry signal does not interfere with the input received to power the miniature implantable device. In one example, the telemetry signal and powering signal are combined into one signal, where the RF telemetry signal is used to modulate the RF powering signal, and thus the implanted device is powered directly by the received telemetry signal; separate electronic subsystems harness the power contained in the signal and interpret the data content of the signal. In other embodiments, the telemetry output rate is at least 8 kilobits per second.

In other implementations, a RF pulse generator system, located externally to the miniature implanted device 100, may store parameters defining the excitation pulses to be applied at electrodes 104, which are transmitted via the second antenna.

Figure 2:
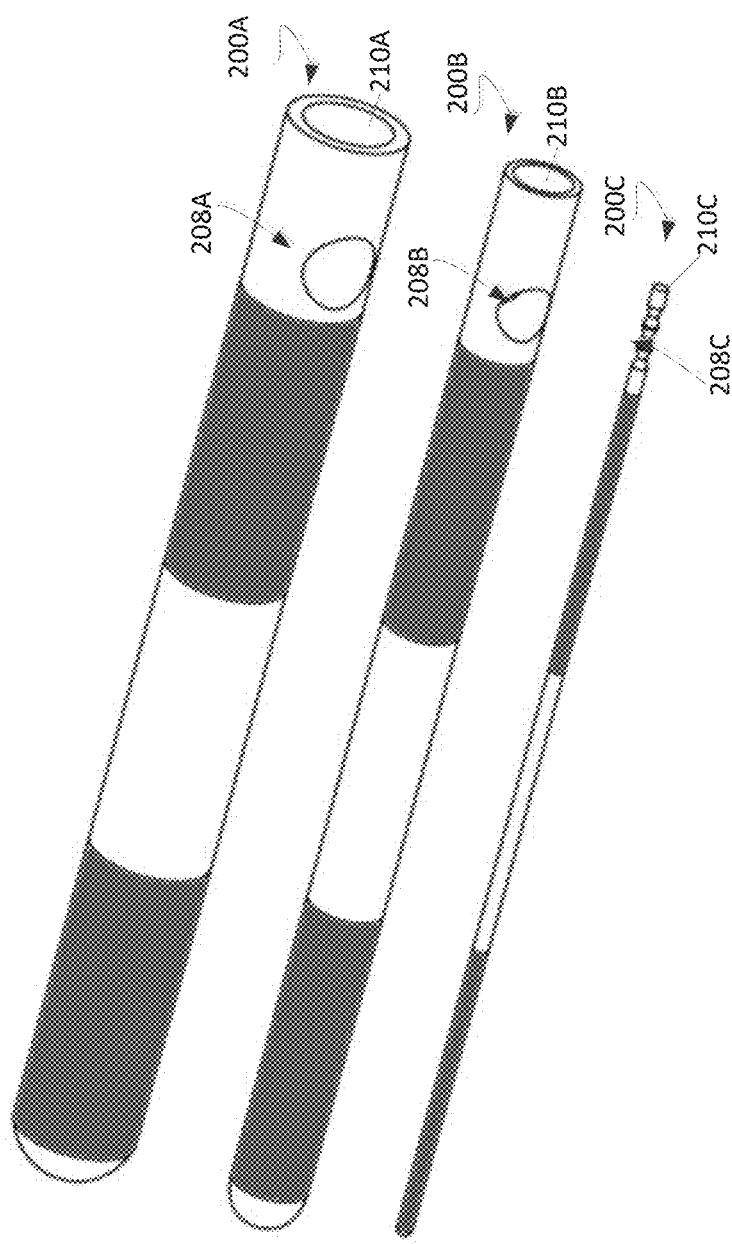
FIG. 2 shows three different sized miniature implantable devices.

FIG. 2 illustrates three examples of miniature implantable devices 200A, 200B, and 200C with various diameters. Miniature implantable device 200A is a miniature implantable device with a diameter of 0.8 mm. Miniature implantable device 200A includes a suturing feature 208A to allow a clinician to suture and anchor implantable miniature implantable device 200A during an implantation procedure. For instance, suture can be passed through the passage of suturing feature 208A and tied to tissue such that the mobility of the implanted device is reduced. As illustrated, implantable device 200A also includes an indentation 210A on the proximal end to allow for mating with a placement stylet during implantation.

Miniature implantable device 200B has a diameter of 0.4 mm and has a suturing feature 208B similar to 208A. Implantable device 200B also includes an indentation 210B on the proximal end to allow for mating with a placement stylet during implantation.

Miniature implantable device 200C has a diameter of 0.1 mm. Miniature implantable device 200C includes a suturing feature 208C in the form of ribs to aid suture in attaching to a surrounding tissue. Implantable device 200C also may include an indentation 210C to allow for mating with a placement stylet during implantation.

Figure 3:
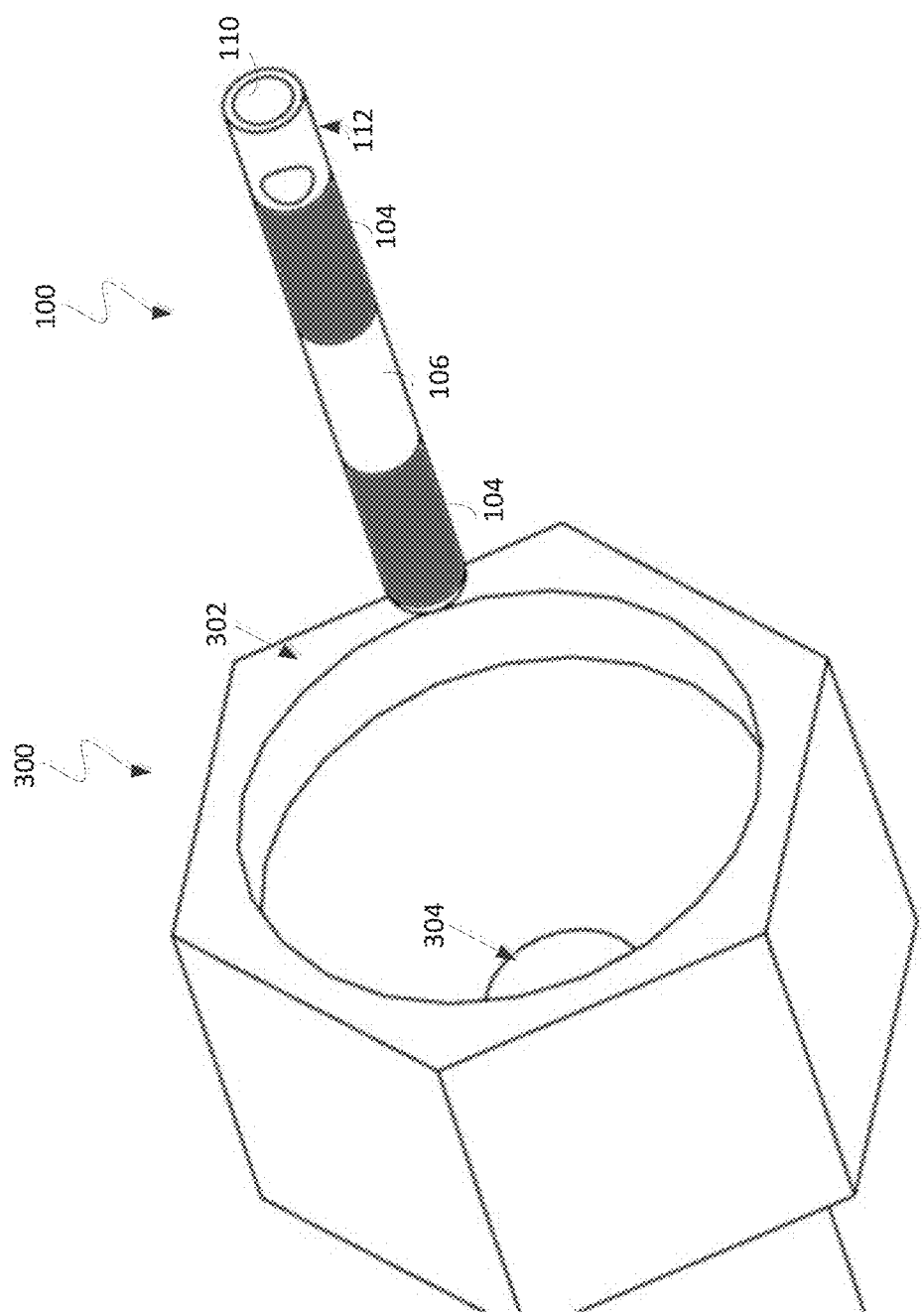
FIG. 3 illustrates a miniature implantable device entering an introducer needle.

FIG. 3 illustrates the miniature wireless device 100 (e.g., a 0.8 mm diameter) entering an 18 gauge needle 300. The distal end (not shown) of miniature implantable device is in position to enter the proximal opening 302 of an 18-gauge needle 300. Miniature implantable device 100 has a diameter small enough to fit into the inner lumen 304 of the needle 300. The illustration may correspond to an implantation of a miniature implantable device with a diameter of 0.8 mm, shown as the implantable device 200A in FIG. 2. Notably, the middle and bottom devices (0.4 mm and 0.1 mm, respectively) shown in FIG. 2 are sized for advancement through introducer needles with even smaller sizes, (e.g., 22 gauge or smaller).

While it is possible to place the device 100 directly into an introducer needle, doing so may not be desirable as the implantable device enclosure may not be as rigid as a guide wire and may not slide easily within the inner lumen of the introducer needle. Yet, a guide wire may not be used because the implantable device may not have a central void through which to mount the guide wire. To improve the ease of placement through an introducer needle, a stylet may be used to provide some rigidity to the miniature device.

Figure 4A:
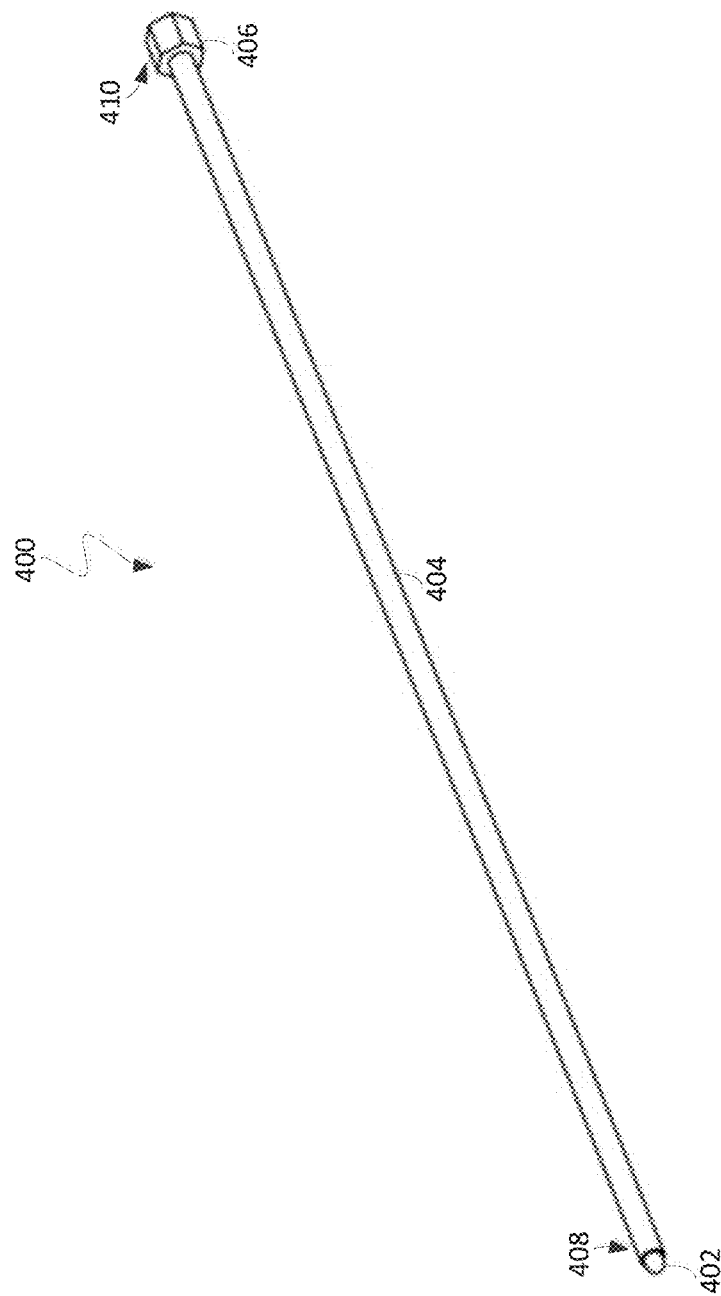
FIG. 4A shows a placement stylet capable of mating with a miniature implantable device.

FIG. 4A shows a placement stylet 400 capable of mating with a miniature implantable device 100 according to some implementations. Placement stylet 400 includes a distal end 408, device body 404, and proximal end 410. Distal end 408 includes a mating feature 402 to allow the placement stylet 400 to engage, for example, miniature implantable device 100. The mating feature 402 is, for example, a convex protrusion that is shaped and sized to mate with the concave indentation 110 of the lead 100. Proximal end 406 includes handle 406 for operator to hold placement stylet 400, for example, during an implantation procedure. Placement stylet 400 can have a longitudinal length of between about 50 mm and about 177 mm. Placement stylet 400 can have an outer diameter in the range from between about 0.1 mm and about 0.9 mm. Placement stylet 400 may be made of a rigid biocompatible material such as stainless steel, titanium, nylon, or polyethylene.

Figure 4B:
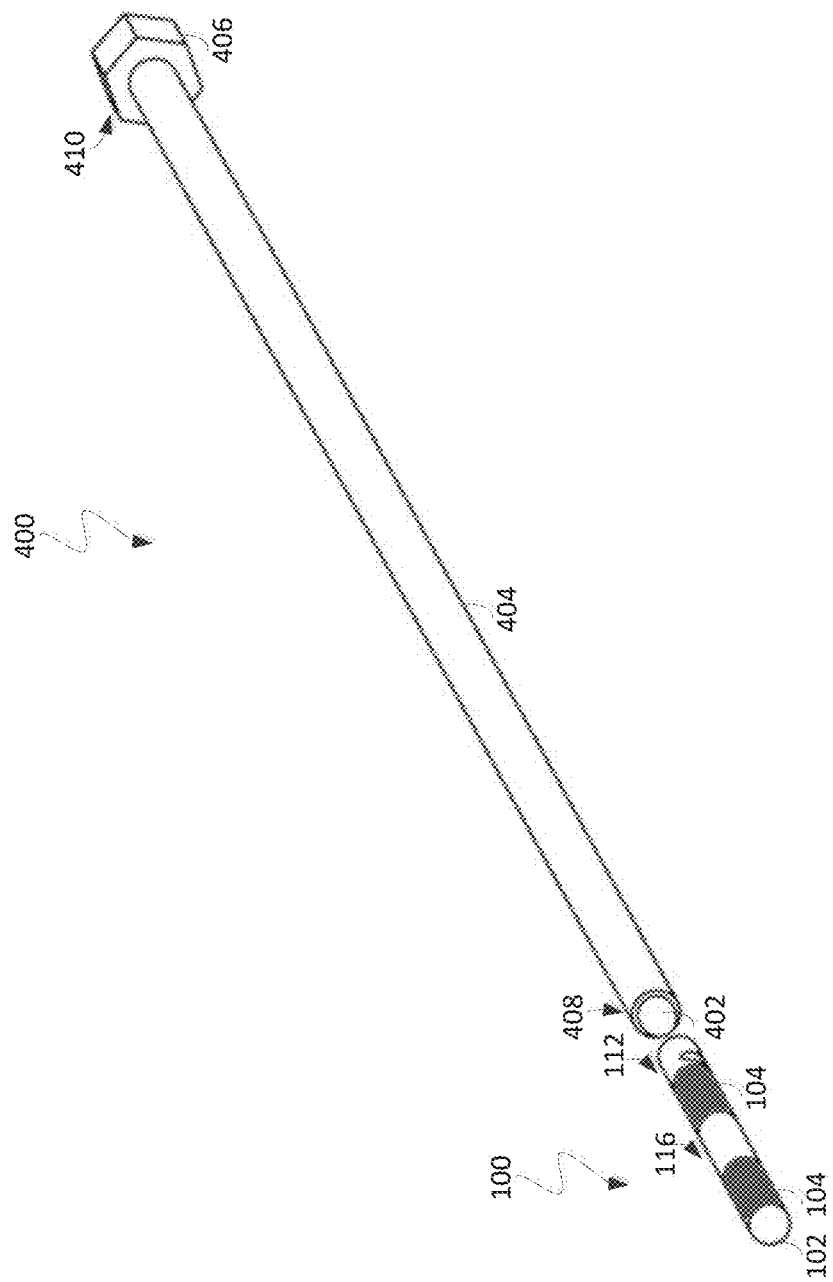
FIG. 4B illustrates a miniature implantable device mated with a placement stylet.

FIG. 4B illustrates a miniature implantable device 100 mated with a placement stylet 400. A clinician may mate the miniature implantable device 100 onto the placement stylet 400. The mating feature 402 on the distal end 408 of the stylet may mate with mating feature 110 on the proximal end 112 of miniature implantable device 100. Mating feature 402 on placement stylet 400 may be semi-spherical in shape, and may provide mechanical gripping for placement stylet 400 to engage the miniature implantable device 100 during placement. Mating feature 402 may be complementary in shape to the shape of mating feature 112 on the proximal end 110 of the device 100. In some configurations, mating feature 402 may be convex in shape. In other configurations, mating feature 402 may include extruded shapes for mating the stylet 400 to the miniature implantable device 100 at mating feature 112, which may have a square, hexagon, star, or an asymmetrical shape. Mating feature 402 may only protrude from the distal end 408 of placement stylet 400 from between 0.1 mm and 1.0 mm and may not fill the entirety of the device body 106 (that is, the feature 402 may only extend partially into device body 106). Mating feature 402 may have a surface material that allows for increased friction to improve the mate between placement stylet 400 and the miniature implantable device 100. Example materials may include silicon or polyurethane.

Figure 5A:
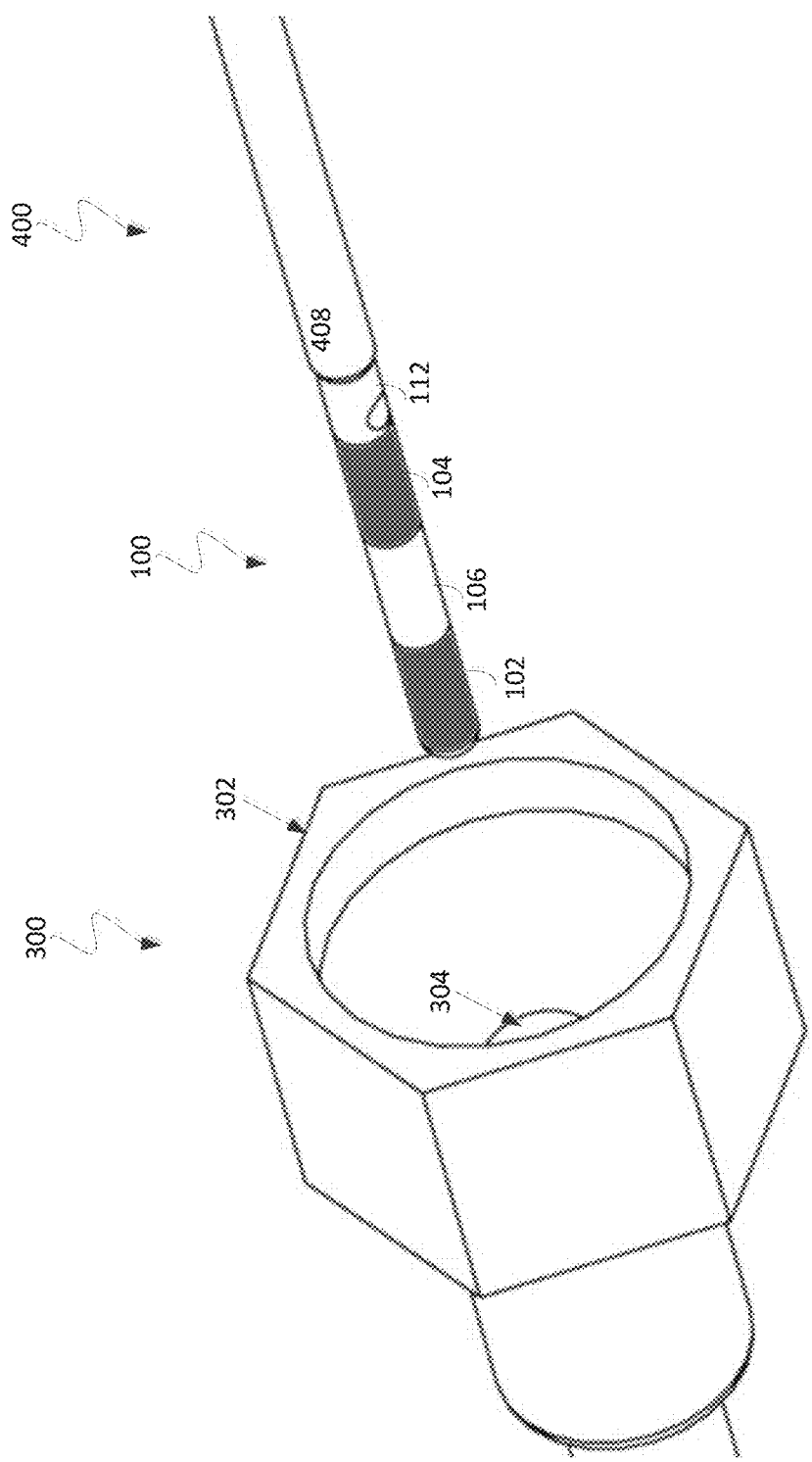
FIG. 5A shows a miniature implantable device mated with a placement stylet entering a proximal opening of an introducer needle.

FIG. 5A illustrates a miniature implantable device 100 mated with a placement stylet 400 entering a proximal opening 302 of needle 300. Miniature implantable device 100 includes lead body 116 that includes electrodes 104 and houses electronic circuitry 106. The proximal end 112 of miniature implantable device 100 is now mated with the distal end 408 of placement stylet 400. As illustrated, after the miniature implantable device 100 has been mated to placement stylet 400, the subassembly of the device 100 with the stylet 400 can now be inserted into an 18 gauge needle 300 or smaller. In particular, the miniature implantable device 100 at the proximal opening 302 of needle 300 is being pushed into position with the placement stylet 400. In fact, the stylet/miniature device subassembly may now slide freely within the inner lumen 304 of the needle 300. The free sliding motion may aid in the surgical placement of the miniature device 100.

Figure 5B:
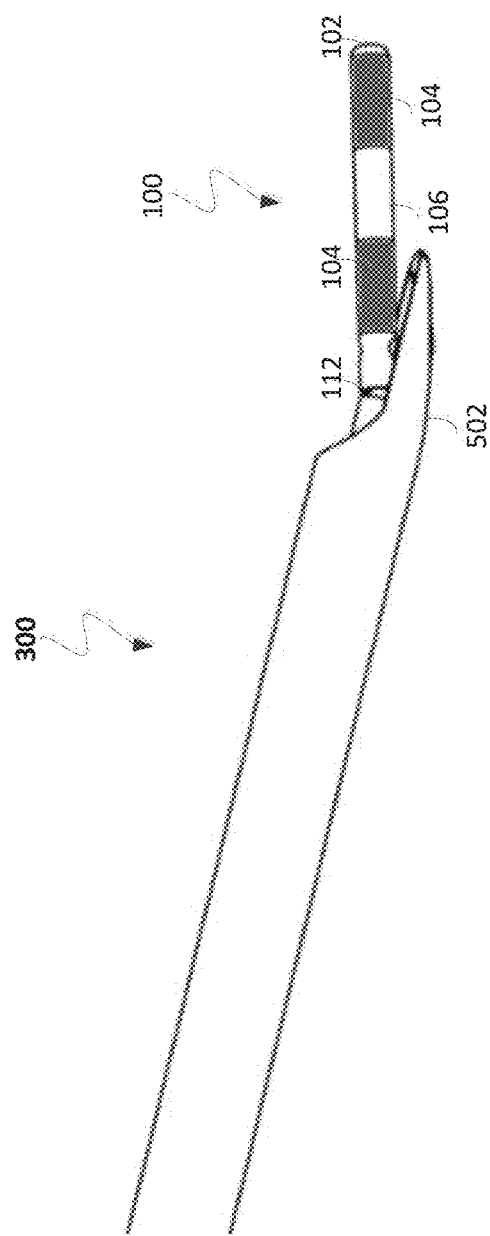
FIGS. 5B and 5C show a miniature implantable device mated with a placement stylet exiting a distal tip of an introducer needle.
Figure 5C:
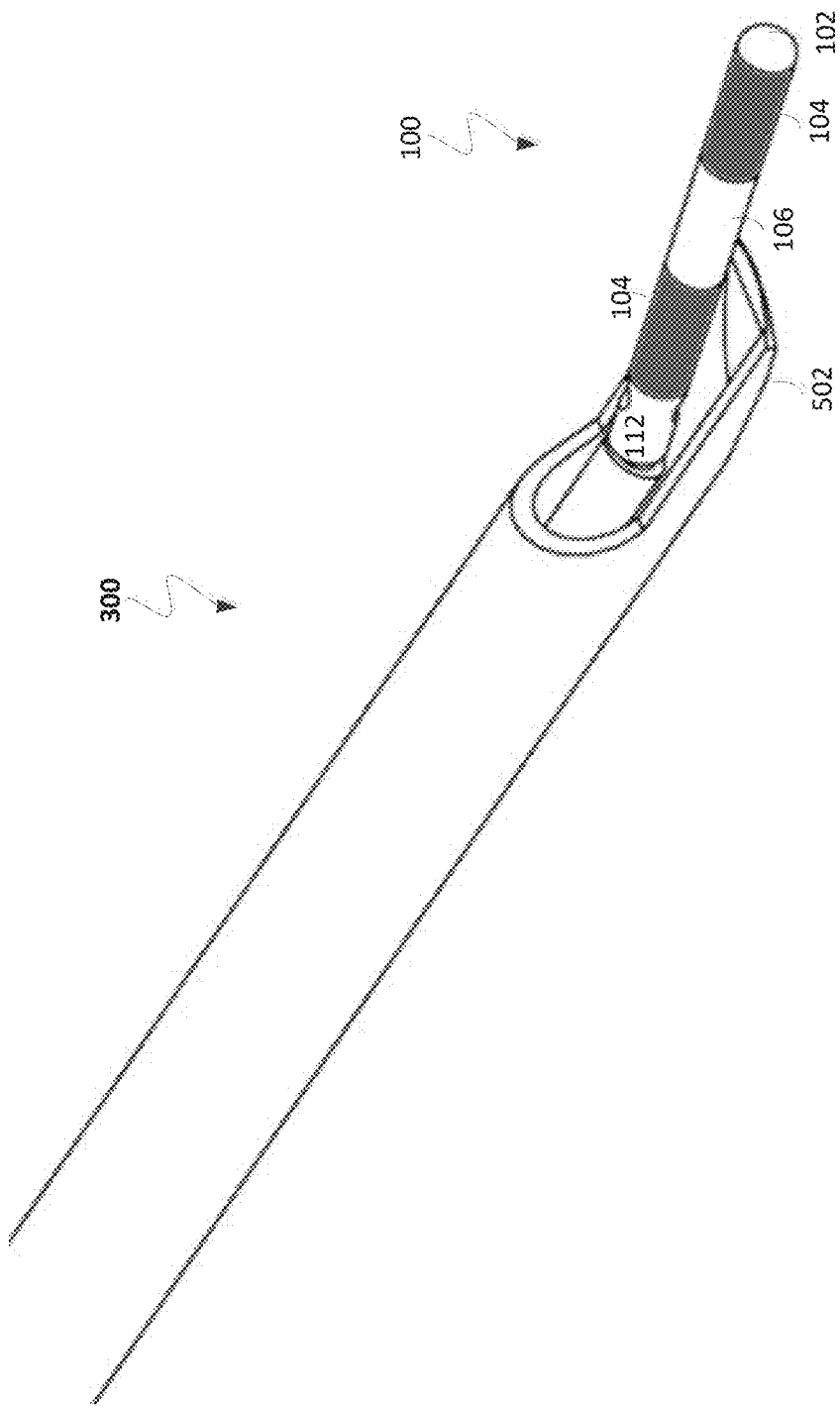

FIGS. 5B and 5C show a miniature implantable device 100 mated with a placement stylet 400 exiting a distal end 502 of needle 300. As discussed above, the miniature implantable device 100 may freely traverse the inner lumen 304 of needle 300 with a size of 18 gauge or smaller. Once the traversal is completed, the miniature implantable device 100 may exit the needle under the pushing force applied on the placement stylet 400 mated to the device 100. As illustrated, rounded tip 102 and body 116 of miniature implantable 100 have exited the distal end 502 of needle 300. The portions of body 116 that include electrodes 104 and electronic circuitry 106 are also shown on FIGS. 5B-5C. The proximal end 112 of miniature implantable 100 is mated to the distal end 408 of placement stylet 400. After the implantable 100 has been placed into a target region, the implantable device 100 may be sutured or anchored in place. Thereafter, the placement stylet 400 may be unmated from the implanted 100. A clinician may then withdraw the placement stylet 400 by pulling the placement stylet 400 out of the patient's body through the needle 300. The placement and withdrawal process may be performed under imaging guidance, such as, for example, X-Ray fluoroscopy, ultrasound fluoroscopy, etc. Once the procedure is completed, needle 300 may be removed.

Figure 6:
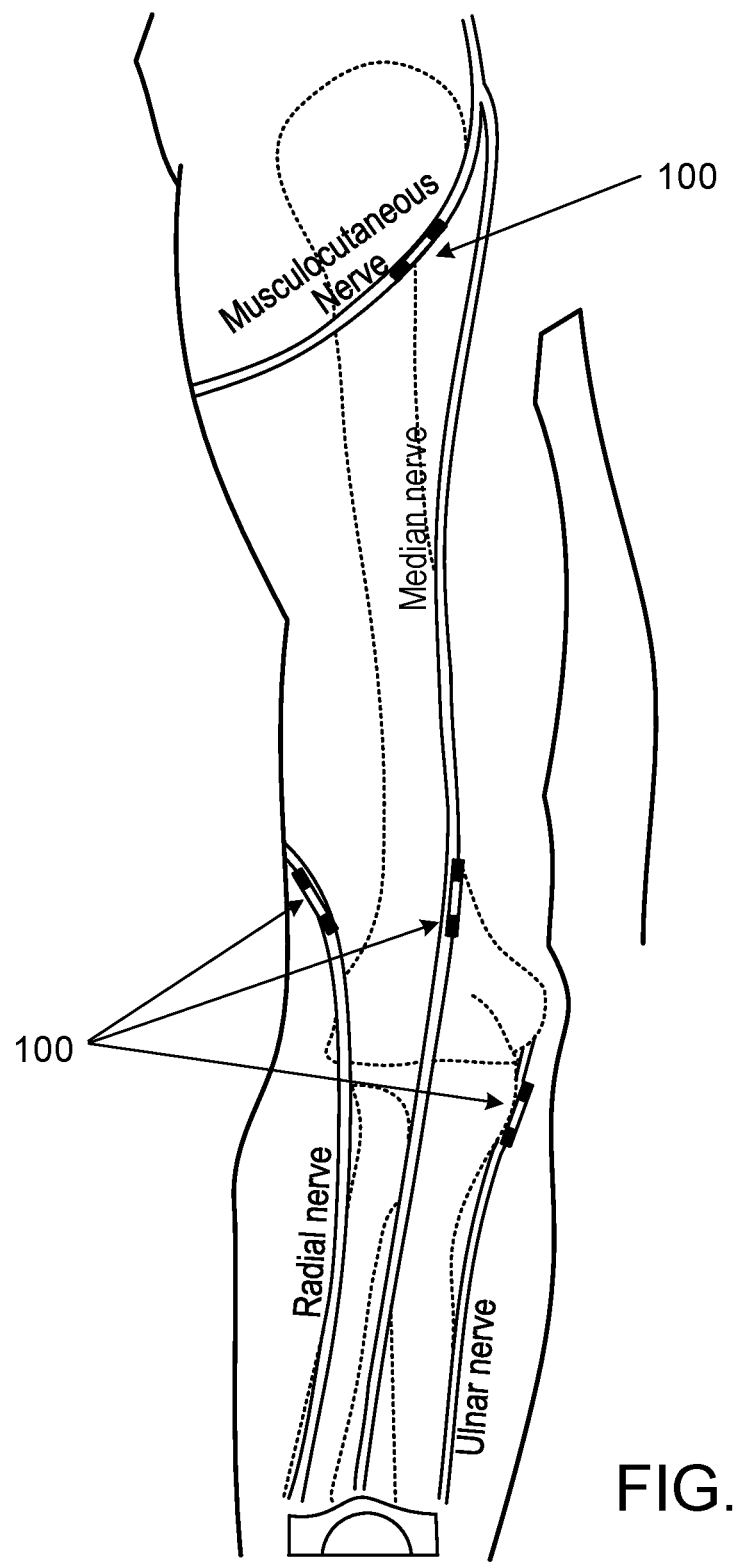
FIG. 6 illustrates the anatomical placement of four miniature implantable devices in the forearm.

FIG. 6 demonstrates the feasibility of placing multiple miniature implantable devices in the anatomical positions of the forearm. The compact size of the miniature implantable device 100 may allow minimally invasive placement procedure, thereby reducing complications during procedure and improving recovery time after procedure. Moreover, the compact size may allow multiple miniature implantable devices to be placed in nearby target areas. As shown in FIG. 6, four miniature implantable devices 100 are placed into the forearm of a patient, one in the upper forearm area and three in the lower forearm area. Each implanted lead may treat a specific nerve branch in the forearm region. Similarly, the miniature implantable devices 100 also may be delivered to treat a neural tissue branching from the spinal column including but not limited to the dorsal root ganglia, traversing, or exiting nerve. The miniature implantable devices 100 may also be delivered to treat peripheral nerve targets such as the radius, ulnar, sciatic, femoral, occipital, or brachial nerves. Given the compact size of the miniature leads, two or more such devices may be placed with pin-point precision to treat multiple nerve branches or peripheral nerve targets at the same time. In particular, two or more such devices may be placed with close proximity within a target area to provide pain-relief therapy to one or more excitable tissues within the target area. For instance, a patient may have one miniature implantable device 100 implanted adjacent to or near a target area. If more therapeutic effect is desired, the patient may have additional miniature implantable devices 100 implanted adjacent to or near the target area to enhance the therapeutic effect.

Figure 7A:
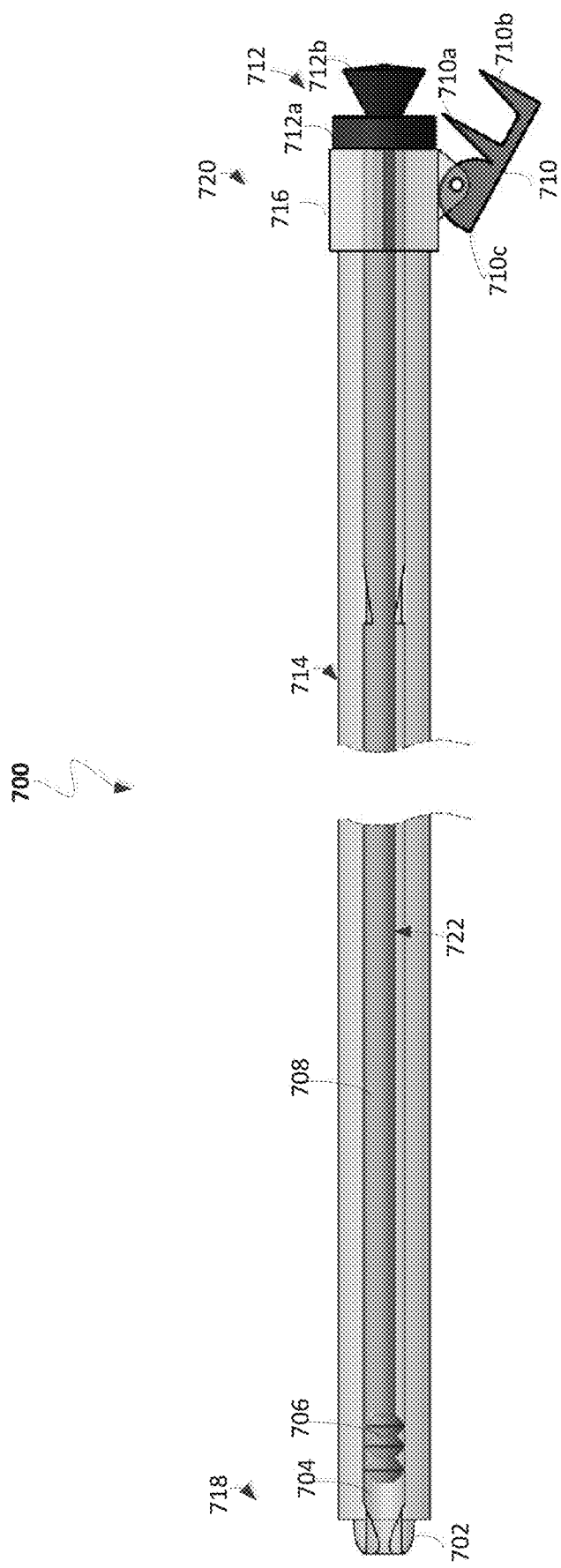
FIG. 7A illustrates an example suction stylet in zero pressure mode.

FIGS. 7A-7E illustrate a suction stylet 700 in various modes of operation. The suction stylet 700 is different from the placement stylet 400 described above. As shown in FIG. 7A, the suction stylet 700 is hollow inside and may have an outer diameter of between about 0.1 mm and 0.9 mm and may have a longitudinal length of between about 50 mm and 170 mm. The suction stylet 700 may have an inner diameter between about 0.05 mm and 0.75 mm. The suction stylet 700 includes distal end 718, stylet body 714, and proximal end 716.

The distal end 718 may include a mating feature 702, chamber 704, and plunger tip 706. Mating feature 702 also may be referred to as the suction tip. In some configurations, mating feature 702 may be semi-spherical in shape and may have a diameter between about 0.05 mm and 0.08 mm. Mating feature 702 on suction stylet 700 may mate to mating feature 110 on miniature wireless lead 100, in a manner similar to the mechanical mating described above. In some instances, a mating force may be provided by a negative air pressure created inside air chamber 704 on suction stylet 700. In particular, by moving the plunger tip 706 along the shaft for inner plunger 708, a negative air pressure may be created in chamber 704.

Stylet body 714 may include inner plunger 708 located inside shaft 722. The inner plunger shaft 722 may have a diameter between about 0.05 mm and 0.75 mm, allowing the plunger 708 to slide inside of the hollow suction stylet 700. The total length of the inner plunger including the inner plunger handle may be between about 50 mm and 170 mm. The inner plunger shaft, when installed, may not protrude beyond the suction tip.

The proximal end 720 of suction stylet 700 may include base 716, handle 712, and locking feature 710. Base 716 may have a diameter of between about 0.1 mm and 0.9 mm depending on the outer diameter of the hollow stylet 700 being utilized. Handle 712 may include cap 712a and tip 712b. Cap 712a closes the tubing of suction stylet 700. Handle tip 712b may be pulled out during a placement procedure. The pulling may cause sliding motion of the plunger 708 inside shaft 722, which creates a negative air pressure in chamber 704. Suction force may be created on suction tip, mating feature 702, so that suction stylet 700 is mated with miniature implantable device 100. Locking mechanism 710 may include spike 710a, spike 710b, and hinge 710c. Hinge 710c is mounted on base 716 and may rotate to engage spikes 710a and 710b with cap 712a, as discussed below.

Figure 7B:
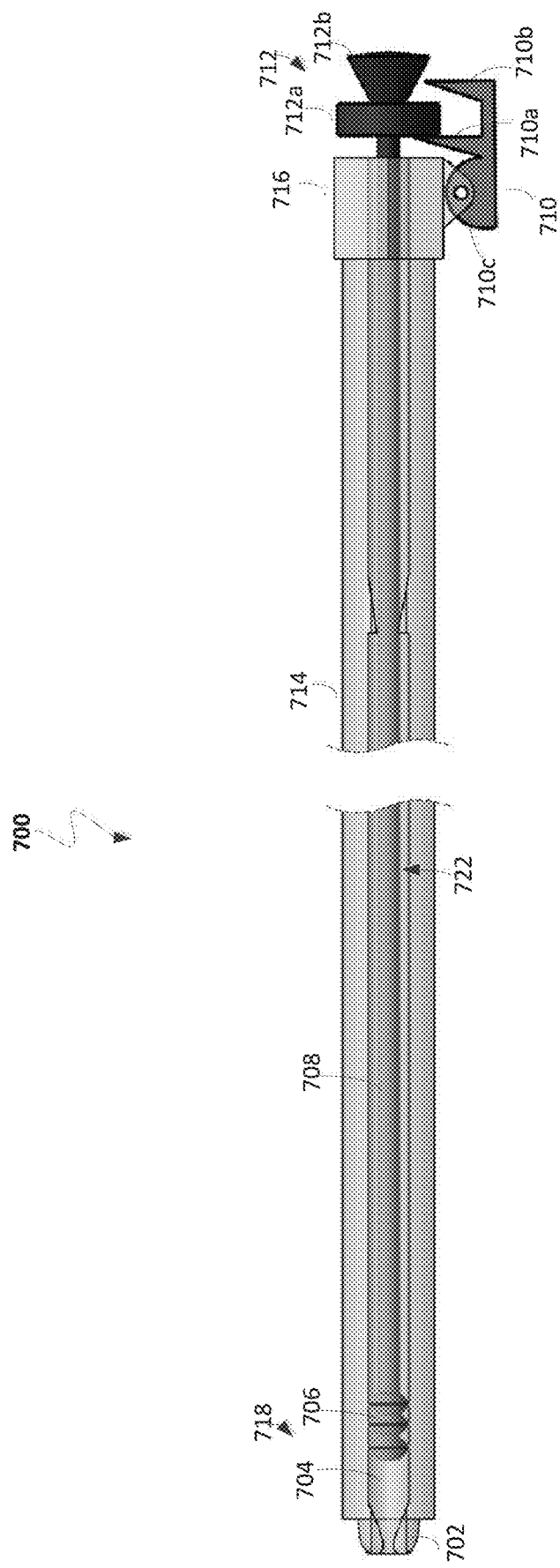
FIG. 7B illustrates the example suction stylet in first level of negative pressure mode.
Figure 7C:
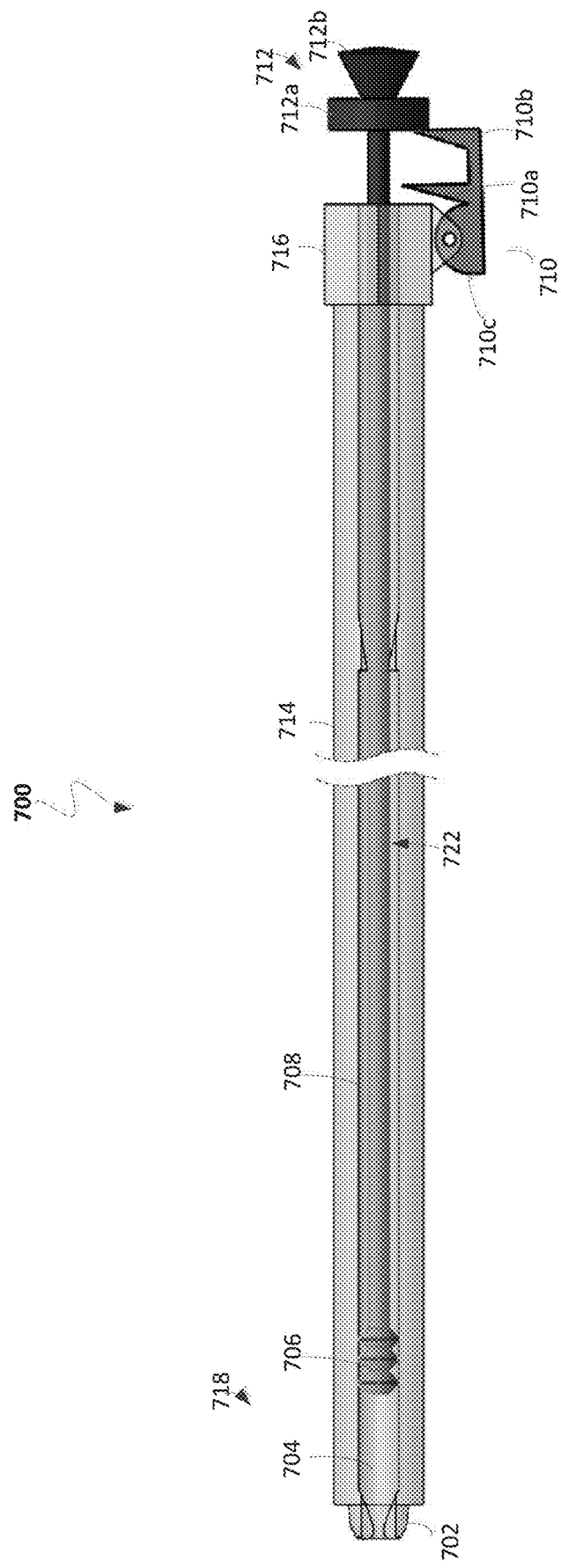
FIG. 7C illustrates the example suction stylet in second level of negative pressure mode.

FIGS. 7A to 7C show the suction stylet without the mating miniature implantable device. As illustrated, the inner plunger 708 may be slid in a translating motion inside shaft 722 to different locations within the hollow stylet 700. Locking mechanism 710 may be used to lock plunger 708 into certain positions.

In particular, FIG. 7A shows the inner plunger 708 in a complete seated condition with respect to the distal end 720 of stylet 700. In this position, no pressure differential may exist between the mating feature 702 and plunger tip 706.

Figure 7D:
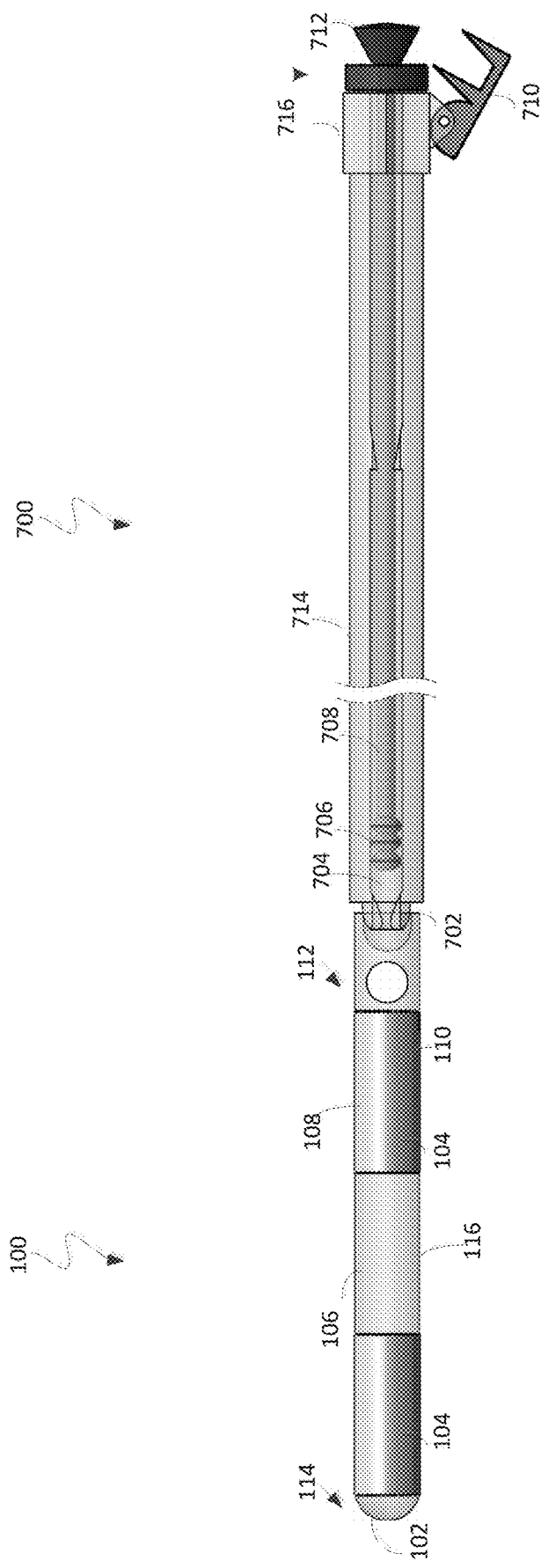
FIG. 7D illustrates an example miniature implantable device when the suction stylet is not active.

FIGS. 7B and 7D shows the inner plunger 708 at stage 1 position, which may be between about 1 mm and 10 mm from mating feature 702 (suction tip) of the hollow stylet 700. FIG. 7B shows suction stylet 700 without the mated miniature implantable device 100, while FIG. 7D shows suction stylet 700 mated with miniature implantable device 100. By pulling the handle tip 712b away from the hollow stylet, a pressure differential may be generated to create a temporary mate between the miniature implantable device 100 and the stylet 100. The mate is between mating feature 102 on miniature implantable device 100 and suction tip 702 on suction stylet 700. Locking mechanism 710, as shown in FIG. 7B, may lock the inner plunger 708 in place by engaging spike 710a between base 716 and cap 712a. Once locked, the pressure differential between suction tip (mating feature 702) and plunger tip 706 may be maintained. This locking mechanism may be adjustable to allow for the inner plunger to be locked in a desired location.

Figure 7E:
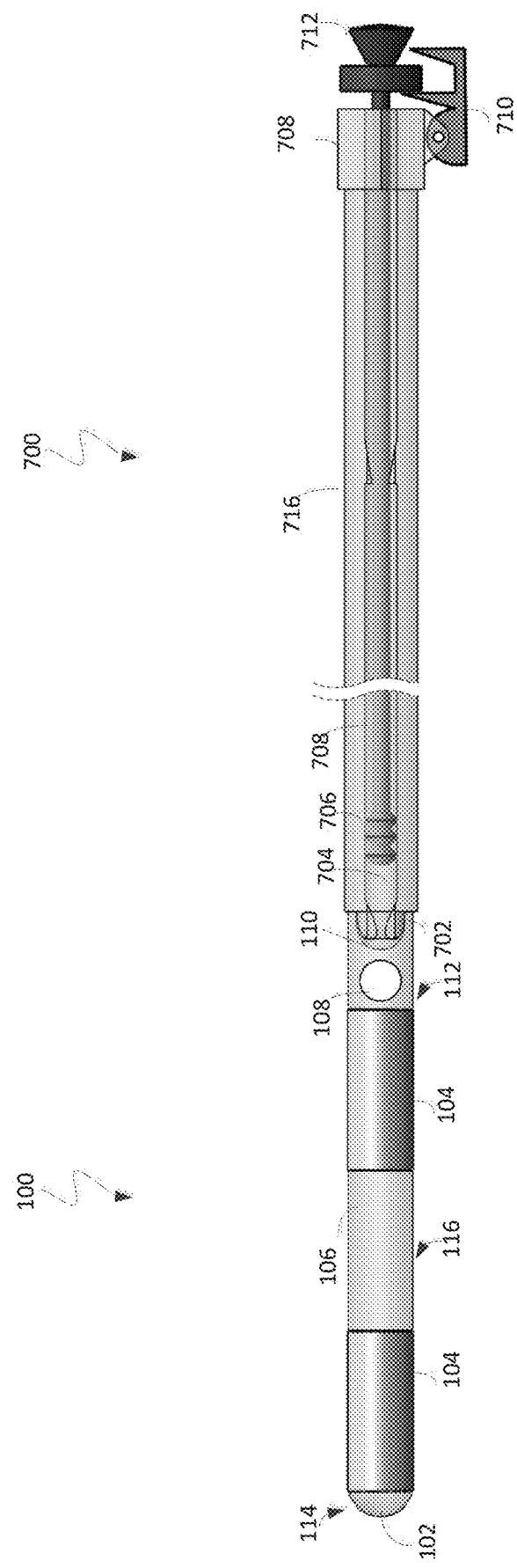
FIG. 7E illustrates an example miniature implantable device when the suction stylet is active.

FIGS. 7C and 7E illustrate the inner plunger 708 being locked into a stage 2 location, which may be between about 2 mm and 30 mm from mating feature 702 (suction tip) of the hollow stylet 700. FIG. 7C shows suction stylet 700 without the mated miniature implantable device 100, while FIG. 7E shows suction stylet 700 mated with miniature implantable device 100. This stage may have a greater pressure differential generated than the stage 1 location depicted in FIG. 7B. In other examples, a suction stylet assembly may have one more locking stages depending on the locking mechanism utilized. An adjustable locking mechanism may allow for infinite locking distance locations.

The suction stylet design may provide the clinician the ability to install and remove the miniature implantable device 100 from a patient. As discussed above, once suction stylet 700 is activated to engage miniature implantable device 100, an assembly of miniature implantable device 100 and suction stylet 700 may be created. The clinician may push the suction stylet to advance the entire assembly, for example, down the inner lumen 304 of needle 300, towards the target site. If the miniature implantable device 100 is already implanted, the clinician can mate the miniature implantable device 100 to the suction tip of the stylet 700, then pull on handle tip 712b. Plunger 708 may slide inside shaft 722, thereby creating a pressure differential between suction tip 702 and plunger tip 706. The pressure differential may engage the miniature implantable device 100, and the clinician may withdraw the suction stylet 700 to take the implanted lead 100 from within the patient.

Figure 8A:
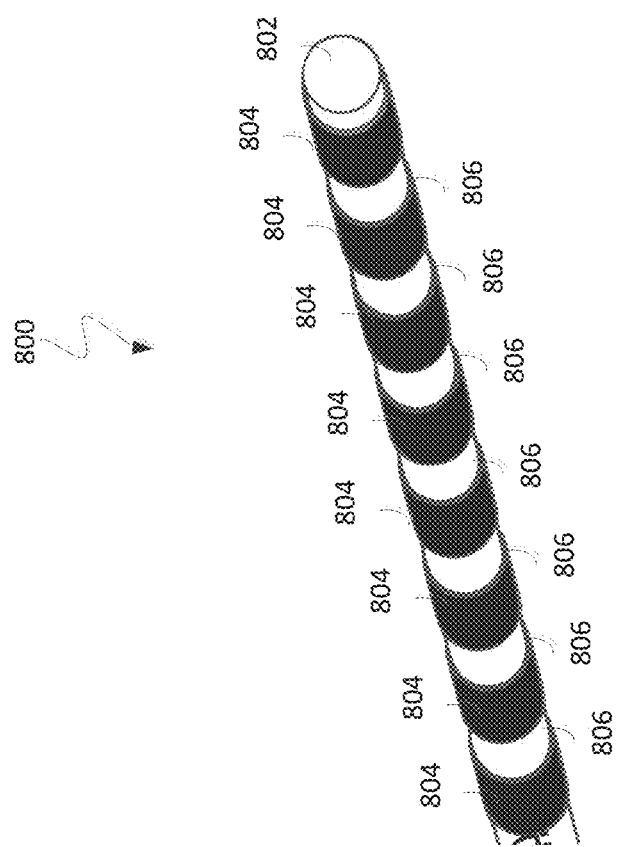
FIG. 8A illustrates a miniature implantable device with multiple recording or stimulating cylindrical electrode pads (eight shown).

FIG. 8A shows cylindrical electrodes 804 (eight (8) shown) on the outside of a lead 800. The outer diameter of lead 800 may be 0.8 cm or smaller. Each cylindrical electrode 804 may operate as a recording or stimulating electrode. A stimulating electrode may apply electric pulses to an excitable tissue to achieve therapeutic effect. A recording electrode may record or sense neural activity from surrounding tissue. In some instances, the electrodes may alternate between stimulating and recording electrodes. In the example shown, the miniature lead 800 is not tethered and not connected to another structure or device for mechanical or electrical interface. One or more electrical flex circuitry may be internal to the miniature lead. The flex circuit may be inside gaps 806, in between electrodes 804. Lead 800 may also include a rounded-tip 802 for easy placement, as well as a mating feature to mate the lead 800 with a stylet, such as those described above.

Figure 8B:
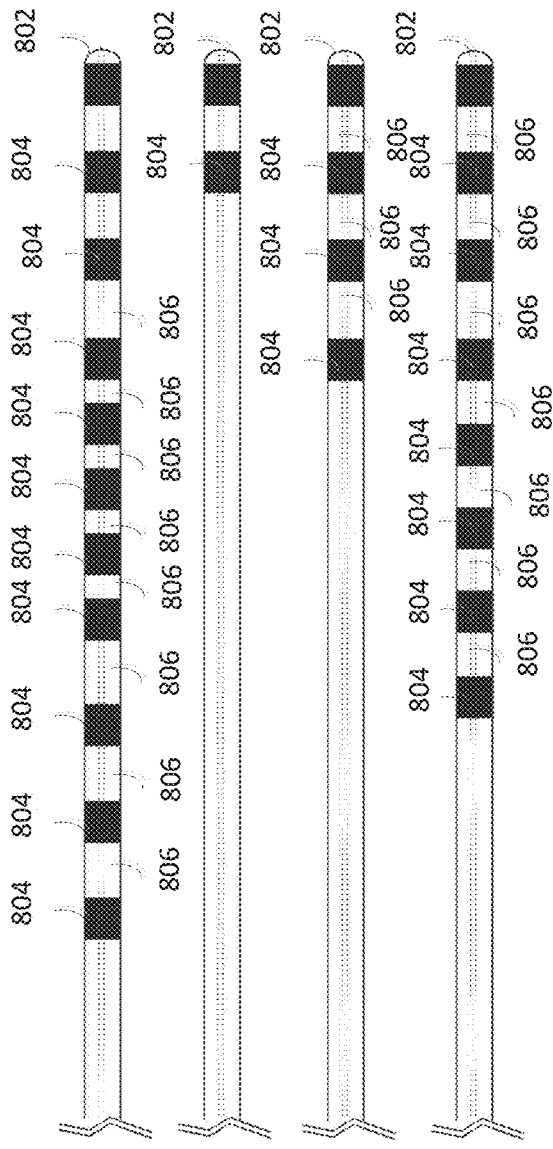
FIG. 8B illustrates various electrode configurations for stimulation and or recording electrodes on the miniature implantable device body, with various inter-electrode spacing options and mixture of recording and stimulation electrode assignments.

FIG. 8B shows four example miniature implantable devices incorporating multiple recording and/or stimulating electrodes 804. The four example leads shown do not have an inner stylet lumen to mount a stylet or a guide wire, but may include a mating feature such as those described above. The recording and/or stimulating electrode pads 804 may couple to a surrounding tissue for recording and/or stimulating. In a recording mode, neural activities of the surrounding tissue may be sensed and capture in electrical signals that encode such neural activities. In a stimulating mode, electric pulses may be applied to the surrounding tissue for pain relief. In some configurations, the electric circuitry may be spaced in between the recording and/or stimulating electrode pads, for example, in gaps 806. As illustrated, example miniature implantable devices 800 may include rounded tip 802 for easy placement.

Figure 8C:
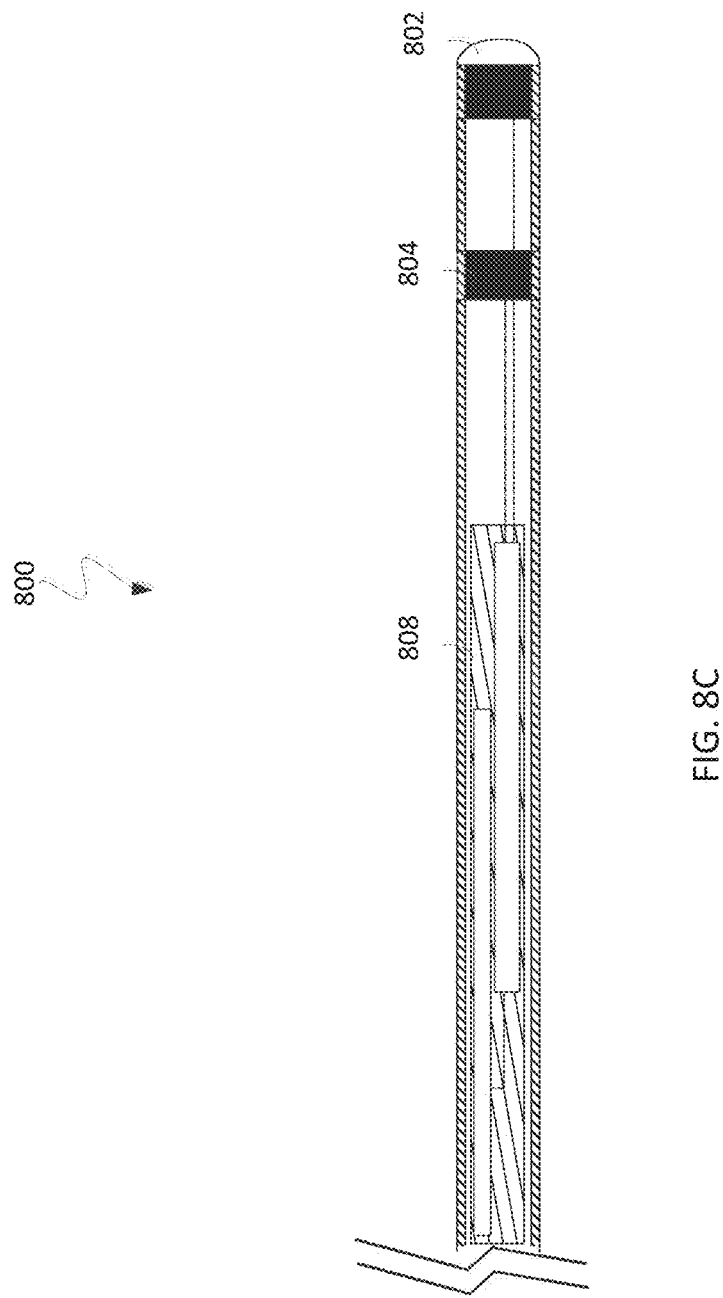
FIG. 8C is a cutout view of a miniature implantable device with stimulation or recording electrodes and the electronic circuitry and wireless power receiver.

FIG. 8C illustrates a miniature implantable device 800 with stimulating and/or recording electrodes 804 located at the distal end of the lead, in the direction of the rounded tip 802. As illustrated, the electronic circuitry 808 is located towards the proximal end of implantable device 800, rather than spaced between the electrodes 802.

For the configurations shown in FIGS. 7A to 7C, the electronic circuitry may provide power to drive the stimulating and/or recording electrodes. As described above, the electric pulses may be created by the electronic circuitry based on the input signal received at the antennas on the implantable devices. The electric pulses may be sent to a stimulating electrode to delivery pain-relief to an excitable tissue. As discussed above, a recording electrode may record neural activities of a surrounding tissue. The electronic circuitry also may route the recorded analog signal to the antennas on the implantable device which may in turn transmit the recorded analog signal to an external controller, located outside the patient body. In some implementations, the recorded analog signal may be processed and transmitted in a manner similar to the telemetry signal described above. For example, the transmission of the recorded analog signal, like the telemetry signal discussed herein, may be powered by the electrical power in the input signal.

Figure 9:
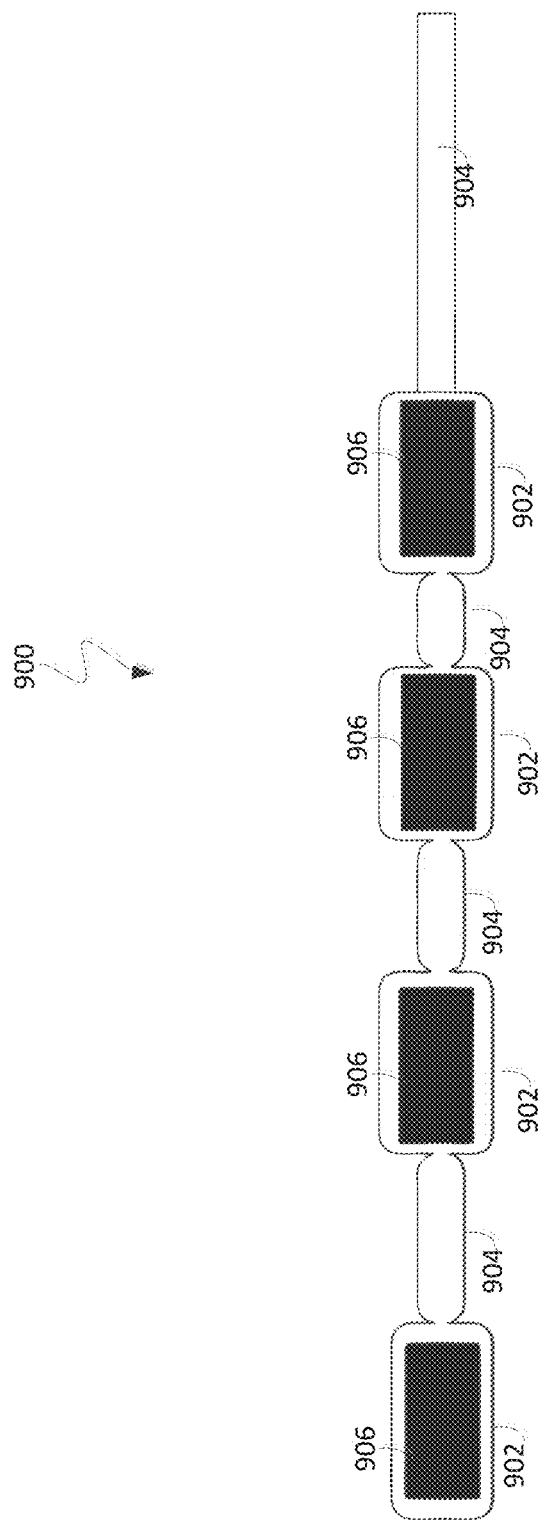
FIG. 9 illustrates a view of a miniature implantable device and a plate electrode configuration for the stimulation or recording pads.

FIG. 9 depicts an example of a lead 900 with each electrode pad 902 configured as a rectangular square. As illustrated, each rectangular square electrode pad 902 may include an electrode 906. Electronic circuitry may be located on structures 904. Electrode 906 may have a surface area of at least 0.06 mm². This implantable device 900 may have a total width from between about 0.5 mm and 0.8 mm. The height of the implantable device 900 may be from between about 0.1 mm and about 0.8 mm. The total length of the implantable device 900 may be from between about 10 mm and about 600 mm. The rectangular electrode pads 902 may have a length from between about 0.5 mm and about 6.0 mm and a width from between about 0.45 mm and about 0.75 mm. The inter-electrode spacing may be from between about 0.1 mm and about 6.0 mm. This implantable device 900 may be suitable for stimulating a relatively large area.

Figure 10:
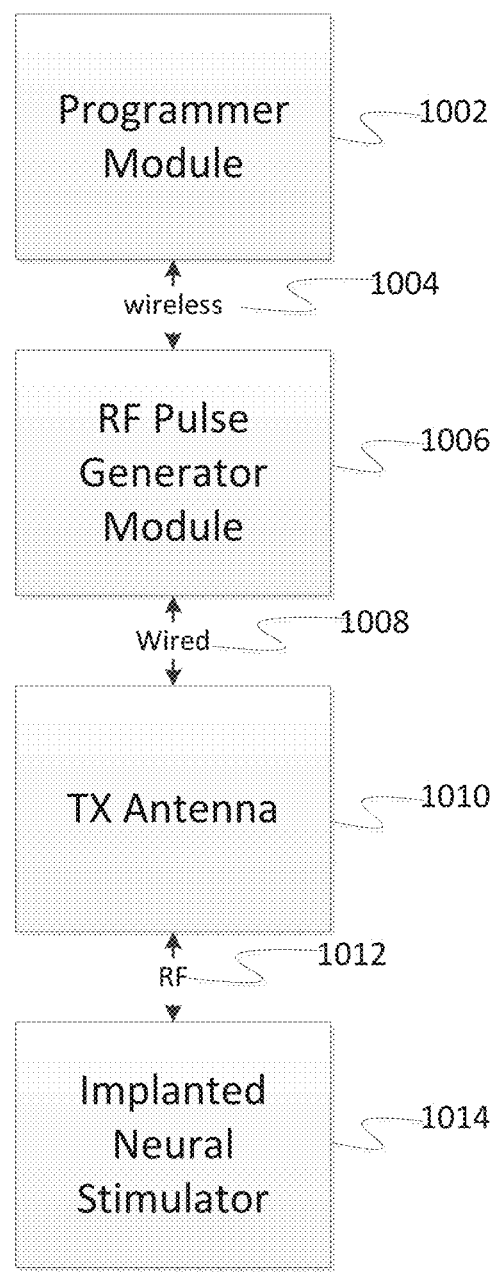
FIG. 10 depicts a high-level diagram of an example of a wireless neural stimulation system.
Figure 11:
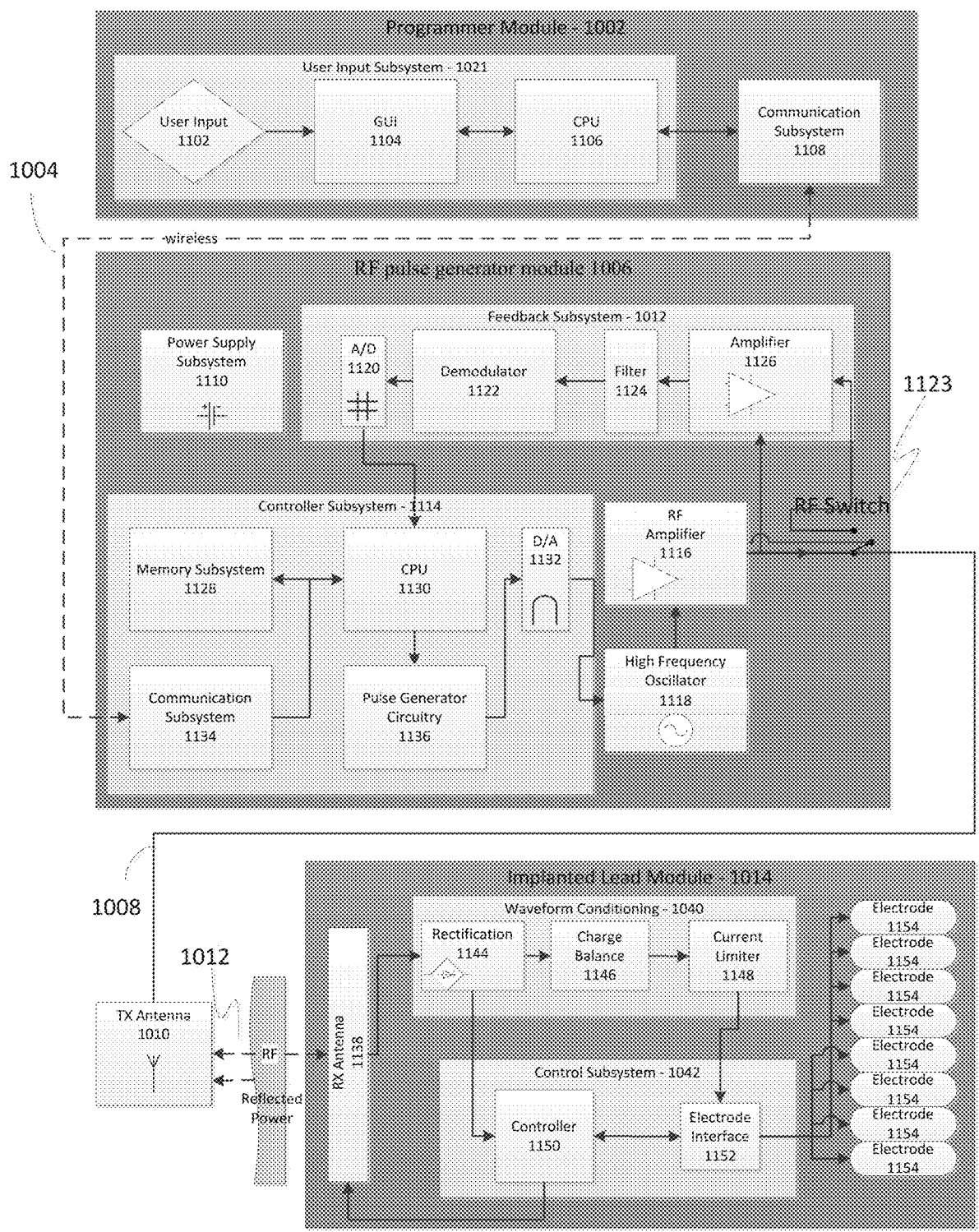
FIG. 11 depicts a detailed diagram of an example of a wireless neural stimulation system.

FIGS. 10 and 11 illustrate an example of a neural stimulation system that may employ the implantable devices described above. These implantable devices may also be referred to as implantable leads.

In particular, FIG. 10 depicts a high-level diagram of an example of a neural stimulation system. The neural stimulation system may include four major components, namely, a programmer module 1002, a RF pulse generator module 1006, a transmit (TX) antenna 1010 (for example, a patch antenna, slot antenna, or a dipole antenna), and an implanted device 1014, which may be a lead such as those described above. The programmer module 1002 may be a computer device, such as a smart phone, running a software application that supports a wireless connection 1014, such as Bluetooth®. The application can enable the user to view the system status and diagnostics, change various parameters, increase/decrease the desired stimulus amplitude of the electrode pulses, and adjust feedback sensitivity of the RF pulse generator module 1006, among other functions.

The RF pulse generator module 1006 may include communication electronics that support the wireless connection 1004, the stimulation circuitry, and the battery to power the generator electronics. In some implementations, the RF pulse generator module 1006 includes the TX antenna embedded into its packaging form factor while, in other implementations, the TX antenna is connected to the RF pulse generator module 1006 through a wired connection 1008 or a wireless connection (not shown). The TX antenna 1010 may be coupled directly to tissue to create an electric field that powers the implanted device 1014. The TX antenna 1010 communicates with the implanted device 1014 through an RF interface. For instance, the TX antenna 1010 radiates an RF transmission signal that is modulated and encoded by the RF pulse generator module 1010. The implanted device 1014 contains one or more antennas, such as dipole antenna (s), to receive and transmit through RF interface 1012. In particular, the coupling mechanism between antenna 1010 and the one or more antennas on the implanted device 1014 is electrical radiative coupling and not inductive coupling. In other words, the coupling is through an electric field rather than a magnetic field.

Through this electrical radiative coupling, the TX antenna 1010 can provide an input signal to the implanted device 1014. This input signal contains energy and may contain information encoding stimulus waveforms to be applied at the electrodes of the implanted device 1014. In some implementations, the power level of this input signal directly determines an applied amplitude (for example, power, current, or voltage) of the one or more electrical pulses created using the electrical energy contained in the input signal. Within the implanted device 1014 are components for demodulating the RF transmission signal, and electrodes to deliver the stimulation to surrounding neuronal tissue.

The RF pulse generator module 1006 can be implanted subcutaneously, or it can be worn external to the body. When external to the body, the RF generator module 1006 can be incorporated into a belt or harness design to allow for electric radiative coupling through the skin and underlying tissue to transfer power and/or control parameters to the implanted device 1014, which can be a passive stimulator. In either event, receiver circuit(s) internal to the device 1014 can capture the energy radiated by the TX antenna 1010 and convert this energy to an electrical waveform. The receiver circuit(s) may further modify the waveform to create an electrical pulse suitable for the stimulation of neural tissue, and this pulse may be delivered to the tissue via electrode pads.

In some implementations, the RF pulse generator module 1006 can remotely control the stimulus parameters (that is, the parameters of the electrical pulses applied to the neural tissue) and monitor feedback from the wireless device 1014 based on RF signals received from the implanted wireless device 1014. A feedback detection algorithm implemented by the RF pulse generator module 1006 can monitor data sent wirelessly from the implanted wireless device 1014, including information about the energy that the implanted wireless device 1014 is receiving from the RF pulse generator and information about the stimulus waveform being delivered to the electrode pads. In order to provide an effective therapy for a given medical condition, the system can be tuned to provide the optimal amount of excitation or inhibition to the nerve fibers by electrical stimulation. A closed loop feedback control method can be used in which the output signals from the implanted wireless device 1014 are monitored and used to determine the appropriate level of neural stimulation current for maintaining effective neuronal activation, or, in some cases, the patient can manually adjust the output signals in an open loop control method.

FIG. 11 depicts a detailed diagram of an example of the neural stimulation system. As depicted, the programming module 1002 may comprise user input system 1102 and communication subsystem 1108. The user input system 1121 may allow various parameter settings to be adjusted (in some cases, in an open loop fashion) by the user in the form of instruction sets. The communication subsystem 1108 may transmit these instruction sets (and other information) via the wireless connection 1004, such as Bluetooth or Wi-Fi, to the RF pulse generator module 1006, as well as receive data from module 1006.

For instance, the programmer module 1002, which can be utilized for multiple users, such as a patient's control unit or clinician's programmer unit, can be used to send stimulation parameters to the RF pulse generator module 1006. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

| Stimulation Parameter | |
| --- | --- |
| Pulse Amplitude: | 0 to 20 mA |
| Pulse Frequency: | 0 to 20,000 Hz |
| Pulse Width: | 0 to 2 ms |

The implantable device 1014 or RF pulse generator module 1014 (which may be a lead such as those described above) may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy.

The programmer module 1002 may be functionally a smart device and associated application. The smart device hardware may include a CPU 1106 and be used as a vehicle to handle touchscreen input on a graphical user interface (GUI) 1104, for processing and storing data.

The RF pulse generator module 1006 may be connected via wired connection 1008 to an external TX antenna 1010. Alternatively, both the antenna and the RF pulse generator are located subcutaneously (not shown).

The signals sent by RF pulse generator module 1006 to the implanted device 1014 may include both power and parameter-setting attributes in regards to stimulus waveform, amplitude, pulse width, and frequency. The RF pulse generator module 1006 can also function as a wireless receiving unit that receives feedback signals from the implanted device 1014. To that end, the RF pulse generator module 1006 may contain microelectronics or other circuitry to handle the generation of the signals transmitted to the device 1014 as well as handle feedback signals, such as those from the device 1014. For example, the RF pulse generator module 1006 may comprise controller subsystem 1114, high-frequency oscillator 1118, RF amplifier 1116, a RF switch, and a feedback subsystem 1112.

The controller subsystem 1114 may include a CPU 1130 to handle data processing, a memory subsystem 1128 such as a local memory, communication subsystem 1134 to communicate with programmer module 1002 (including receiving stimulation parameters from programmer module), pulse generator circuitry 1136, and digital/analog (D/A) converters 1132.

The controller subsystem 1114 may be used by the patient and/or the clinician to control the stimulation parameter settings (for example, by controlling the parameters of the signal sent from RF pulse generator module 1006 to device 1014). These parameter settings can affect, for example, the power, current level, or shape of the one or more electrical pulses. The programming of the stimulation parameters can be performed using the programming module 1002, as described above, to set the repetition rate, pulse width, amplitude, and waveform that will be transmitted by RF energy to the receive (RX) antenna 1138, typically a dipole antenna (although other types may be used), in the wireless implanted device 1114. The clinician may have the option of locking and/or hiding certain settings within the programmer interface, thus limiting the patient's ability to view or adjust certain parameters because adjustment of certain parameters may require detailed medical knowledge of neurophysiology, neuroanatomy, protocols for neural modulation, and safety limits of electrical stimulation.

The controller subsystem 1114 may store received parameter settings in the local memory subsystem 1128, until the parameter settings are modified by new input data received from the programming module 1002. The CPU 1106 may use the parameters stored in the local memory to control the pulse generator circuitry 1136 to generate a stimulus waveform that is modulated by a high frequency oscillator 1118 in the range from 300 MHz to 8 GHz. The resulting RF signal may then be amplified by RF amplifier 1126 and then sent through an RF switch 1123 to the TX antenna 1010 to reach through depths of tissue to the RX antenna 1138.

In some implementations, the RF signal sent by TX antenna 1010 may simply be a power transmission signal used by the device 1014 to generate electric pulses. In other implementations, a telemetry signal may also be transmitted to the device 1014 to send instructions about the various operations of the device 1014. The telemetry signal may be sent by the modulation of the carrier signal (through the skin if external, or through other body tissues if the pulse generator module 1006 is implanted subcutaneously). The telemetry signal is used to modulate the carrier signal (a high frequency signal) that is coupled onto the implanted antenna(s) 1138 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 1123 may be a multipurpose device such as a dual directional coupler, which passes the relatively high amplitude, extremely short duration RF pulse to the TX antenna 1010 with minimal insertion loss while simultaneously providing two low-level outputs to feedback subsystem 1112; one output delivers a forward power signal to the feedback subsystem 1112, where the forward power signal is an attenuated version of the RF pulse sent to the TX antenna 1010, and the other output delivers a reverse power signal to a different port of the feedback subsystem 212, where reverse power is an attenuated version of the reflected RF energy from the TX Antenna 1010.

During the on-cycle time (when an RF signal is being transmitted to the device 1014), the RF switch 1123 is set to send the forward power signal to feedback subsystem. During the off-cycle time (when an RF signal is not being transmitted to the device 1014), the RF switch 1123 can change to a receiving mode in which the reflected RF energy and/or RF signals from the device 1014 are received to be analyzed in the feedback subsystem 1112.

The feedback subsystem 1112 of the RF pulse generator module 1006 may include reception circuitry to receive and extract telemetry or other feedback signals from the device 1014 and/or reflected RF energy from the signal sent by TX antenna 1010. The feedback subsystem may include an amplifier 1126, a filter 1124, a demodulator 1122, and an A/D converter 1120.

The feedback subsystem 1112 receives the forward power signal and converts this high-frequency AC signal to a DC level that can be sampled and sent to the controller subsystem 1114. In this way the characteristics of the generated RF pulse can be compared to a reference signal within the controller subsystem 1114. If a disparity (error) exists in any parameter, the controller subsystem 1114 can adjust the output to the RF pulse generator 1006. The nature of the adjustment can be, for example, proportional to the computed error. The controller subsystem 1114 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, when TX antenna 1010 has perfectly matched impedance to the tissue that it contacts, the electromagnetic waves generated from the RF pulse generator 1006 pass unimpeded from the TX antenna 1010 into the body tissue. However, in real-world applications a large degree of variability may exist in the body types of users, types of clothing worn, and positioning of the antenna 1010 relative to the body surface. Since the impedance of the antenna 1010 depends on the relative permittivity of the underlying tissue and any intervening materials, and also depends on the overall separation distance of the antenna from the skin, in any given application there can be an impedance mismatch at the interface of the TX antenna 1010 with the body surface. When such a mismatch occurs, the electromagnetic waves sent from the RF pulse generator 1006 are partially reflected at this interface, and this reflected energy propagates backward through the antenna feed.

The dual directional coupler RF switch 1123 may prevent the reflected RF energy propagating back into the amplifier 1126, and may attenuate this reflected RF signal and send the attenuated signal as the reverse power signal to the feedback subsystem 1112. The feedback subsystem 1112 can convert this high-frequency AC signal to a DC level that can be sampled and sent to the controller subsystem 1114. The controller subsystem 1114 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 1114 can measure the reflected-power ratio in real time, and according to preset thresholds for this measurement, the controller subsystem 1114 can modify the level of RF power generated by the RF pulse generator 1006. For example, for a moderate degree of reflected power the course of action can be for the controller subsystem 1114 to increase the amplitude of RF power sent to the TX antenna 1010, as would be needed to compensate for slightly non-optimum but acceptable TX antenna coupling to the body. For higher ratios of reflected power, the course of action can be to prevent operation of the RF pulse generator 1006 and set a fault code to indicate that the TX antenna 1010 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can lead to unwanted heating of internal components, and this fault condition means the system cannot deliver sufficient power to the implanted wireless neural stimulator and thus cannot deliver therapy to the user.

The controller 1142 of the device 1014 may transmit informational signals, such as a telemetry signal, through the antenna 1138 to communicate with the RF pulse generator module 1006 during its receive cycle. For example, the telemetry signal from the device 1014 may be coupled to the modulated signal on the dipole antenna(s) 1138, during the on and off state of the transistor circuit to enable or disable a waveform that produces the corresponding RF bursts necessary to transmit to the external (or remotely implanted) pulse generator module 1006. The antenna(s) 1138 may be connected to electrodes 1154 in contact with tissue to provide a return path for the transmitted signal. An A/D (not shown) converter can be used to transfer stored data to a serialized pattern that can be transmitted on the pulse modulated signal from the internal antenna(s) 1138 of the neural stimulator.

A telemetry signal from the implanted wireless device 1014 may include stimulus parameters such as the power or the amplitude of the current that is delivered to the tissue from the electrodes. The feedback signal can be transmitted to the RF pulse generator module 1016 to indicate the strength of the stimulus at the nerve bundle by means of coupling the signal to the implanted RX antenna 1138, which radiates the telemetry signal to the external (or remotely implanted) RF pulse generator module 1006. The feedback signal can include either or both an analog and digital telemetry pulse modulated carrier signal. Data such as stimulation pulse parameters and measured characteristics of stimulator performance can be stored in an internal memory device within the implanted device 1014, and sent on the telemetry signal. The frequency of the carrier signal may be in the range of at 300 MHz to 8 GHz.

In the feedback subsystem 1112, the telemetry signal can be down modulated using demodulator 1122 and digitized by being processed through an analog to digital (A/D) converter 1120. The digital telemetry signal may then be routed to a CPU 1130 with embedded code, with the option to reprogram, to translate the signal into a corresponding current measurement in the tissue based on the amplitude of the received signal. The CPU 1130 of the controller subsystem 1114 can compare the reported stimulus parameters to those held in local memory 1128 to verify the stimulator(s) 1014 delivered the specified stimuli to tissue. For example, if the stimulator reports a lower current than was specified, the power level from the RF pulse generator module 1006 can be increased so that the implanted neural stimulator 1014 will have more available power for stimulation. The implanted neural stimulator 1014 can generate telemetry data in real time, for example, at a rate of 8 kbits per second. All feedback data received from the implanted lead module 1014 can be logged against time and sampled to be stored for retrieval to a remote monitoring system accessible by the health care professional for trending and statistical correlations.

The sequence of remotely programmable RF signals received by the internal antenna(s) 1138 may be conditioned into waveforms that are controlled within the implantable device 1014 by the control subsystem 1142 and routed to the appropriate electrodes 1154 that are placed in proximity to the tissue to be stimulated. For instance, the RF signal transmitted from the RF pulse generator module 1006 may be received by RX antenna 1138 and processed by circuitry, such as waveform conditioning circuitry 1140, within the implanted wireless device 1014 to be converted into electrical pulses applied to the electrodes 1154 through electrode interface 1152. In some implementations, the implanted device 1014 contains between two to sixteen electrodes 1154.

The waveform conditioning circuitry 1140 may include a rectifier 1144, which rectifies the signal received by the RX antenna 1138. The rectified signal may be fed to the controller 1142 for receiving encoded instructions from the RF pulse generator module 1006. The rectifier signal may also be fed to a charge balance component 1146 that is configured to create one or more electrical pulses based such that the one or more electrical pulses result in a substantially zero net charge at the one or more electrodes (that is, the pulses are charge balanced). The charge-balanced pulses are passed through the current limiter 1148 to the electrode interface 1152, which applies the pulses to the electrodes 1154 as appropriate.

The current limiter 1148 insures the current level of the pulses applied to the electrodes 1154 is not above a threshold current level. In some implementations, an amplitude (for example, current level, voltage level, or power level) of the received RF pulse directly determines the amplitude of the stimulus. In this case, it may be particularly beneficial to include current limiter 1148 to prevent excessive current or charge being delivered through the electrodes, although current limiter 1148 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 1148 may act as a charge limiter that limits a characteristic (for example, current or duration) of the electrical pulses so that the charge per phase remains below a threshold level (typically, a safe-charge limit).

In the event the implanted wireless device 1014 receives a "strong" pulse of RF power sufficient to generate a stimulus that would exceed the predetermined safe-charge limit, the current limiter 1148 can automatically limit or "clip" the stimulus phase to maintain the total charge of the phase within the safety limit. The current limiter 1148 may be a passive current limiting component that cuts the signal to the electrodes 1154 once the safe current limit (the threshold current level) is reached. Alternatively, or additionally, the current limiter 1148 may communicate with the electrode interface 1152 to turn off all electrodes 1154 to prevent tissue damaging current levels.

A clipping event may trigger a current limiter feedback control mode. The action of clipping may cause the controller to send a threshold power data signal to the pulse generator 1006. The feedback subsystem 1112 detects the threshold power signal and demodulates the signal into data that is communicated to the controller subsystem 1114. The controller subsystem 1114 algorithms may act on this current-limiting condition by specifically reducing the RF power generated by the RF pulse generator, or cutting the power completely. In this way, the pulse generator 1006 can reduce the RF power delivered to the body if the implanted wireless neural stimulator 1014 reports it is receiving excess RF power.

The controller 1150 of the device 1105 may communicate with the electrode interface 1152 to control various aspects of the electrode setup and pulses applied to the electrodes 1154. The electrode interface 1152 may act as a multiplex and control the polarity and switching of each of the electrodes 1154. For instance, in some implementations, the wireless stimulator 1006 has multiple electrodes 1154 in contact with tissue, and for a given stimulus the RF pulse generator module 1006 can arbitrarily assign one or more electrodes to 1) act as a stimulating electrode, 2) act as a return electrode, or 3) be inactive by communication of assignment sent wirelessly with the parameter instructions, which the controller 1150 uses to set electrode interface 1152 as appropriate. It may be physiologically advantageous to assign, for example, one or two electrodes as stimulating electrodes and to assign all remaining electrodes as return electrodes.

Also, in some implementations, for a given stimulus pulse, the controller 1150 may control the electrode interface 1152 to divide the current arbitrarily (or according to instructions from pulse generator module 1006) among the designated stimulating electrodes. This control over electrode assignment and current control can be advantageous because in practice the electrodes 1154 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T start and terminated at a time T_final, and this time course may be synchronized across all stimulating and return electrodes; further, the frequency of repetition of this stimulus cycle may be synchronous for all the electrodes. However, controller 1150, on its own or in response to instructions from pulse generator 1006, can control electrode interface 1152 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 1150 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 1150 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 1150 was configured to match the repetition rate for set B to that of set A, for such a case the controller 1150 can specify the relative start times of the stimulus cycles to be coincident in time or to be arbitrarily offset from one another by some delay interval.

In some implementations, the controller 1150 can arbitrarily shape the stimulus waveform amplitude, and may do so in response to instructions from pulse generator 1006. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 1150 can increase or decrease the level of current at any time during the stimulus phase and/or during the charge-balancing phase. Thus, in some implementations, the controller 1150 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the device 1014 may include a charge-balancing component 1146. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units of uC/cm$^2$. In order to avoid the irreversible electrochemical reactions such as pH change, electrode dissolution as well as tissue destruction, no net charge should appear at the electrode-electrolyte interface, and it is generally acceptable to have a charge density less than 30 uC/cm$^2$. Biphasic stimulating current pulses ensure that no net charge appears at the electrode after each stimulation cycle and the electrochemical processes are balanced to prevent net dc currents. The device 1014 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 1146 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment of the present invention, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless device 1014 may create a drive-waveform envelope that follows the envelope of the RF pulse received by the receiving dipole antenna(s) 1138. In this case, the RF pulse generator module 1006 can directly control the envelope of the drive waveform within the wireless device 1014, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted device 1014 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the RF pulse generator module 1006, and in others this control may be administered internally by circuitry onboard the wireless device 1014, such as controller 1150. In the case of onboard control, the amplitude and timing may be specified or modified by data commands delivered from the pulse generator module 1006.

A number of implementations have been described. Nevertheless, it will be understood that various modifications may be made. Accordingly, other implementations are within the scope of the following claims.

What is claimed is:

1. A method for treating neurological pain, the method comprising:
    inserting an introducer needle through a percutaneous incision site on a body, the introducer needle being of gauge 18 or smaller;
    coupling a first mating feature at a distal end of an elongate member of a stylet to a second mating feature of an implantable device that is configured to receive a wireless signal and to generate one or more electrical pulses from the wireless signal for exciting a tissue within the body, wherein the implantable device further comprises:
        a cylindrical body defining a longitudinal axis of the implantable device,
        a plurality of electrodes distributed along the cylindrical body and configured to deliver the one or more electrical pulses, and
        an anchoring feature adjacent the cylindrical body and disposed proximal to the plurality of electrodes for securing the implantable device to the tissue,
    wherein the second mating feature is disposed proximal to the anchoring feature, disposed in-line with the longitudinal axis of the implantable device, and defines a proximal end of the implantable device,
    advancing the stylet and the implantable device together as an assembly to the tissue within the body through a lumen of the introducer needle; and
    applying the one or more electrical pulses to one or more electrodes of the plurality of electrodes of the implantable device to modulate the tissue within the body.

2. The method of claim 1, wherein the implantable device is wirelessly powered and further comprises:
    a first antenna configured to receive, from a second antenna and through electrical radiative coupling, an input signal carrying electrical energy, the second antenna being physically separate from the implantable device; and
    one or more circuits electrically connected to the first antenna, the one or more circuits configured to:
        create the one or more electrical pulses, the one or more electrical pulses suitable for stimulation of the tissue using the electrical energy; and
        supply the one or more electrical pulses to the one or more electrodes of the plurality of electrodes.

3. The method of claim 1, wherein the stylet comprises a placement stylet.

4. The method of claim 1, wherein the stylet comprises a suction stylet.

5. The method of claim 4, further comprising activating the suction stylet by pulling a plunger in the suction stylet to create a negative pressure in an air chamber of the suction stylet to mate the suction stylet with the implantable device.

6. The method of claim 1, further comprising withdrawing the assembly of the implantable device and the stylet from the tissue.

7. The method of claim 1, wherein the implantable device is a first implantable device, the plurality of electrodes is a plurality of first electrodes, and the one or more electrical pulses are one or more first electrical pulses, the method further comprising:
    advancing a second implantable device to the tissue within the body through the lumen of the introducer needle; and
    applying one or more second electrical pulses to one or more second electrodes of a plurality of second electrodes of the second implantable device to modulate the tissue within the body.

8. The method of claim 1, wherein the introducer comprises a tuohy needle.

9. The method of claim 1, wherein the anchoring feature comprises a passageway through which a suture can be passed to secure the implantable device to the tissue.

10. The method of claim 1, wherein the implantable device further comprises an antenna for receiving the wireless signal.

11. The method of claim 1, wherein one of the first and second mating features has a convex profile and one of the first and second mating features has a concave profile.

12. The method of claim 1, wherein each of the plurality of electrodes is cylindrical in shape and is arranged in-line with the cylindrical body.

13. The method of claim 1, wherein the anchoring feature is positioned along the longitudinal axis of the implantable device.

14. The method of claim 1, wherein the implantable device further comprises a smooth, round tip that defines a distal end of the implantable device.

15. The method of claim 1, wherein a rigidity of the stylet facilitates passage of the assembly of the stylet and the implantable device through the lumen of the introducer needle and the percutaneous incision site.

16. The method of claim 1, wherein the assembly of the stylet and the implantable device is sized and shaped to be passed through the lumen of the introducer needle.

* * * * *